(12) United States Patent
Zhang et al.

(10) Patent No.: US 8,886,319 B2
(45) Date of Patent: Nov. 11, 2014

(54) MRI SIGNAL FILTERING FOR IMPLANTABLE MEDICAL DEVICE

(75) Inventors: Jin Zhang, Porter Ranch, CA (US); J. Christopher Moulder, Portland, OR (US); George I. Isaac, Port Hueneme, CA (US); Gabriel A. Mouchawar, Valencia, CA (US); Peter Boileau, Valencia, CA (US); Ingmar Viohl, Milwaukee, WI (US)

(73) Assignee: Pacesetter, Inc., Sylmar, CA (US)

( * ) Notice: Subject to any disclaimer, the term of this patent is extended or adjusted under 35 U.S.C. 154(b) by 1035 days.

(21) Appl. No.: 12/617,532

(22) Filed: Nov. 12, 2009

(65) Prior Publication Data

US 2011/0112599 A1 May 12, 2011

(51) Int. Cl.
*A61N 1/08* (2006.01)
*G01R 33/28* (2006.01)
*A61N 1/37* (2006.01)
*A61N 1/375* (2006.01)
*A61N 1/365* (2006.01)
*G01R 33/36* (2006.01)

(52) U.S. Cl.
CPC ........... *G01R 33/288* (2013.01); *A61N 1/36521* (2013.01); *A61N 1/3718* (2013.01); *A61N 1/3754* (2013.01); *G01R 33/3685* (2013.01)
USPC ............................................... 607/36; 607/37

(58) Field of Classification Search
CPC ............... A61N 1/3718; A61N 1/3754; G01R 33/3685; H01R 2201/12
USPC ...................................................... 607/36, 37
See application file for complete search history.

(56) References Cited

U.S. PATENT DOCUMENTS

| | | |
|---|---|---|
| 4,712,555 A | 12/1987 | Thornander et al. |
| 4,788,980 A | 12/1988 | Mann et al. |
| 4,940,052 A | 7/1990 | Mann et al. |
| 4,944,298 A | 7/1990 | Sholder |
| 5,466,254 A | 11/1995 | Helland |
| 5,476,483 A | 12/1995 | Bornzin et al. |
| 6,209,764 B1 | 4/2001 | Hartlaub et al. |
| 6,901,292 B2 | 5/2005 | Hrdlicka et al. |
| 7,164,950 B2 | 1/2007 | Kroll et al. |
| 2003/0204217 A1 | 10/2003 | Greatbatch |
| 2005/0197677 A1 | 9/2005 | Stevenson |
| 2006/0085043 A1 | 4/2006 | Stevenson |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0123949 A1 | 5/2007 | Dabney et al. |
| 2008/0132986 A1* | 6/2008 | Gray et al. ............. 607/122 |
| 2011/0029036 A1* | 2/2011 | Yamamoto et al. ...... 607/36 |

* cited by examiner

*Primary Examiner* — Tammie K Heller

(57) ABSTRACT

A filtering scheme for an implantable medical device mitigates potentially adverse effects that may be caused by MRI-induced signals. In some aspects filtering is provided to attenuate MRI-induced signals on an implanted cardiac lead that is coupled to an implanted device. In some aspects the filter may be configured to complement a capacitor circuit (e.g., a feedthrough capacitor) that reduces the amount of EMI that enters the implanted device via the cardiac lead. In some implementations the filter consists of a LC tank circuit and a series LC circuit, where the LC tank circuit is in series with the cardiac lead and a cardiac stimulation circuit and the series LC circuit is in a shunt configuration across the cardiac stimulation circuit.

20 Claims, 14 Drawing Sheets

MRI SIGNAL FILTERING FOR IMPLANTABLE MEDICAL DEVICE

TECHNICAL FIELD

This application relates generally to implantable medical devices and, more specifically, but not exclusively to filtering MRI signals.

BACKGROUND

An implantable medical device may connect to one or more implantable conductors that are outside of the device. For example, an implantable cardiac rhythm management device (e.g., a pacemaker, a defibrillator, or a cardioverter) may connect to one or more leads implanted in or near the heart of a patient to monitor cardiac function and provide therapy for a patient who suffers from cardiac arrhythmia. For example, the implantable device may process signals received via implanted cardiac leads to track the type and timing of native cardiac signals. In the event cardiac events are not occurring at appropriate times or undesired cardiac events are detected, the implantable device may apply stimulation signals to the heart via the implanted cardiac leads in an attempt to restore normal cardiac rhythm.

Studies have found, however, that magnetic resonance imaging ("MRI") scans of a patient may cause an implantable medical device implanted in the patient to malfunction. For example, in some cases time-varying magnetic fields generated during an MRI scan may induce currents in an implanted lead that may, in turn, stimulate (i.e., cause capture of) cardiac tissue. In addition, a relatively large current and/or voltage may be generated at an external interface of an implantable medical device as a result of MRI scanning. In such cases, signals may enter internal circuitry of the implantable medical device and cause the device to malfunction. In some cases, MRI-induced signals may cause heating problems in the implanted lead.

MRI-induced stimulating currents may arise in different ways. In some cases pulsed magnetic gradients used during MRI scanning may induce voltage in an implanted cardiac lead connected to an implanted device. If such voltage appears across sufficiently low impedance, current will flow which may stimulate the heart. In some cases, pulses of amplitude modulated radiofrequency ("RF") energy from MRI scanning (e.g., with a carrier at 64 MHz or 128 MHz) may be rectified within an implantable device and exit the implantable device as a lower frequency demodulated signal on the implanted lead. This lower frequency signal may then travel to the patient's heart via the implanted lead and potentially cause unintended pacing. In some cases, this unintended pacing may cause cardiac fibrillation.

In view of the above, a physician may elect to not prescribe MRI scanning for a patient who has an implanted medical device. Consequently, such a patient may receive suboptimal treatment. Accordingly, a need exists for MRI-compatible implantable medical devices that are immune to the influence of MRI magnetic fields. Ideally, a patient who has an implanted MRI-compatible medical device should have no extra restrictions going under an MRI scan as compared to a patient who does not have such an implanted device.

SUMMARY

A summary of several sample aspects of the disclosure follows. For convenience, a particular aspect or several aspects of the disclosure may be referred to herein using terminology such as "in some aspects."

The disclosure relates in some aspects to an RF filtering system for an implantable medical device that mitigates potentially adverse effects that may result from MRI scanning of a patient. In some aspects the RF filtering system attenuates signals that are induced on an implanted cardiac lead as a result of MRI scanning. For example, the RF filtering system may reduce gradient-induced currents in the lead and attenuate RF energy such that rectification in the device is sufficiently reduced. In this way, the RF filtering system may prevent MRI-induced signals from stimulating cardiac tissue, may prevent the device from malfunctioning, and may prevent lead overheating. Moreover, the MRI-induced signals may be attenuated without significantly attenuating intended cardiac stimulation (e.g., pacing) signals that may be generated by the device. An MRI-compatible implantable medical device may thus be provided through the use of such an RF filtering system.

The disclosure relates in some aspects to a filter that is embedded within an implantable medical device to filter out certain RF frequencies in the event the device is in an MRI environment. In some implementations such a filter may comprise a feedthrough filter. For example, the filter may be located between internal circuitry of the device and a connector located external to the device that connects to the cardiac lead. Here, some or all of the filter circuits may be provide within or adjacent to a conductor feedthrough provided in the housing of the device.

The disclosure relates in some aspects to a filter that includes an LC tank (i.e., parallel LC) resonant circuit and a series LC resonant circuit. In some aspects the filter is designed in conjunction with a feedthrough capacitor to optimize the filter for high RF immunity under MRI-related frequencies or other frequencies. The filter may be designed to utilize superimposition and inter-coupling effects of the resonant circuits to provide highly effective filter performance. Moreover, this may be achieved while providing a very reliable circuit that may be manufactured at a relatively low cost (e.g., through the use of passive components).

The LC tank circuit is provided in series with the cardiac lead and an internal circuit of an implantable medical device, while the series LC circuit is in a shunt configuration across the internal circuit. These LC circuits are configured to attenuate MRI-induced signals (e.g., in the 64 MHz range, the 128 MHz range, some other frequency range, or a combination of these ranges). For example, the LC tank circuit may have high impedance at MRI-related frequencies while the series LC circuit will have low impedance at MRI-related frequencies. In this way, any signals induced in the cardiac lead by MRI scanning may be significantly attenuated before they enter the cardiac stimulation circuit.

A capacitor circuit (e.g., a feedthrough capacitor) may be provided before the filter to reduce the amount of electromagnetic interference (EMI) that enters the implanted device via the cardiac lead. In some aspects, this capacitor circuit may be configured to reduce the duration of any MRI-induced signals in the cardiac lead.

The disclosure relates in some aspects to an RF filter system comprising multiple series LC circuits shunted across an internal circuit of an implantable medical device. Here, each series LC circuit may be configured so that it has a resonant frequency that causes RF signals induced by MRI scanning to flow through the series LC circuit rather than the internal circuit.

The disclosure relates in some aspects to an RF filter system embedded within an implantable cardiac lead, whereby the RF filter system filters out certain RF frequencies (e.g., when the lead is in an MRI environment). For example, current limiting and/or voltage limiting maybe implemented in a cardiac lead and an implantable medical device to reduce heating of the lead and to attenuate induced RF current and voltage that may enter an internal circuit of the implantable medical device. Here, a current limiting circuit (e.g., LC tank circuit) may be implemented at the head of the cardiac lead to reduce current flow to patient tissue. At the device side, a current and voltage limiting circuit may be employed. A large valued series impedance (e.g., impedance at a particular MRI frequency) at the device side will limit the RF current, and a small valued shunt impedance (e.g., impedance at a particular MRI frequency) will work as a voltage divider to limit the RF voltage at the device.

In some implementations the cardiac lead may be configured with multiple LC tank circuits at its distal end to attenuate MRI-induced signals that may otherwise stimulate cardiac tissue. Here, each LC tank circuit may be configured so that it has a resonant frequency that provides high impedance to RF signals induced by MRI scanning.

BRIEF DESCRIPTION OF THE DRAWINGS

These and other features, aspects, and advantages will be more fully understood when considered with respect to the following detailed description, the appended claims, and the accompanying drawings, wherein:

Figure 1:
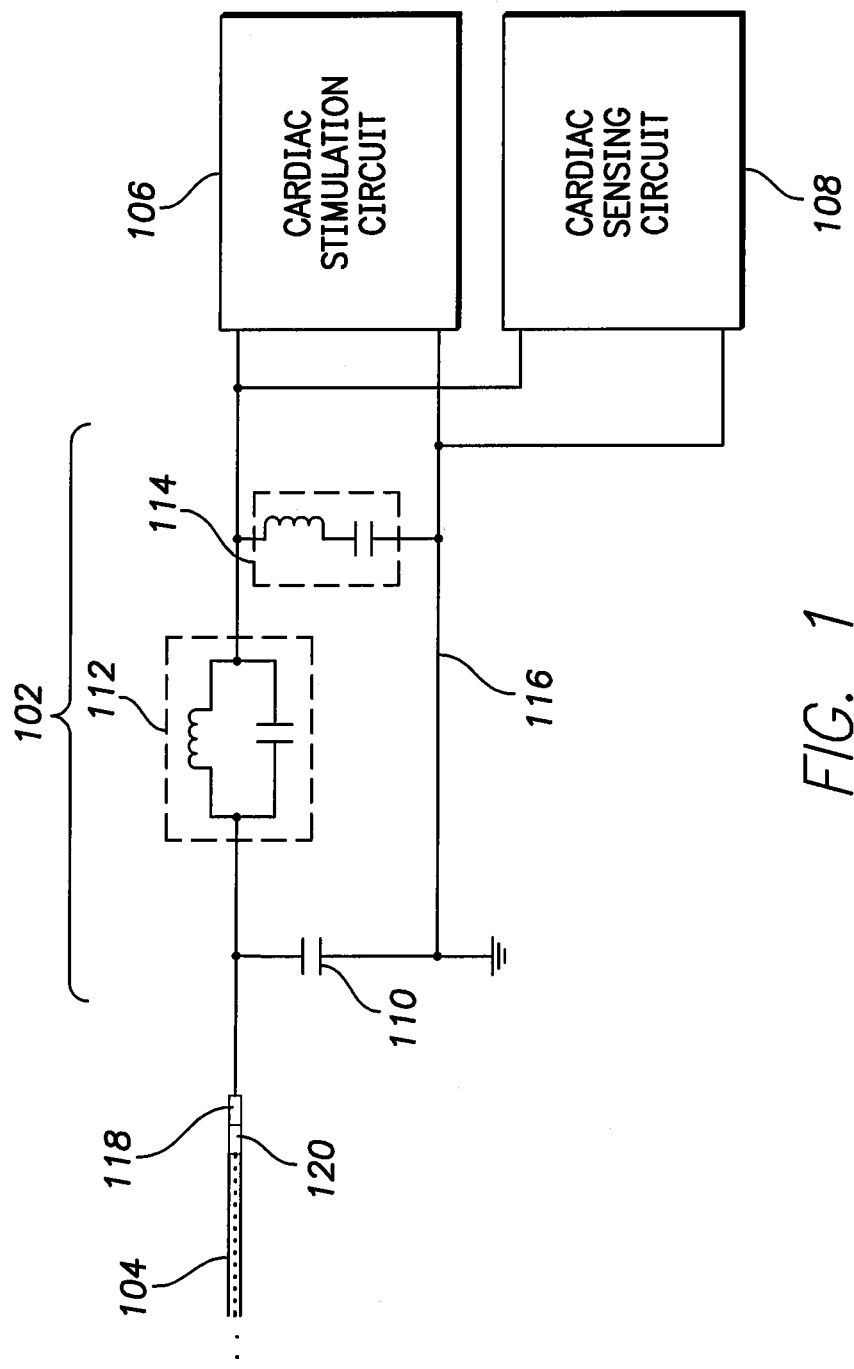
FIG. 1 is a simplified diagram of an embodiment of a circuit that filters MRI-induced signals for an implantable medical device.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 depicts a simplified diagram of a filter circuit 102 that is configured to couple an implantable cardiac lead 104 with internal circuitry of an implantable medical device. In this example, the circuitry includes a cardiac stimulation circuit 106 (e.g., a circuit for providing pacing pulses) and a cardiac sensing circuit 108. For convenience, only a proximal portion of the lead 104 is shown.

The filter circuit 102 includes a feedthrough filter circuit 110, an LC tank circuit 112 (e.g., comprising an inductor and a capacitor in parallel), and a shunt series LC circuit 114 (e.g., comprising an inductor and a capacitor in series). These elements are configured to, for example, reduce gradient-induced currents in the lead 104 and attenuate RF energy (for both the RF voltage and current), particularly at frequencies associated with MRI, that may otherwise enter the implantable medical device. Here, the LC tank circuit 112 is configured in series with respect to the lead 104 and the illustrated internal circuitry of the implantable medical device, while the shunt series LC circuit 114 is configured in parallel across terminals of the internal circuitry. Conductor 116 is a circuit ground (e.g., coupled to the case of the implantable medical device).

Typically, the feedthrough filter circuit 110 is implemented as a capacitor. That is, at least a portion of the capacitance may be implemented within a hermetic feedthrough assembly which is part of the housing for an implantable medical device. The feedthrough filter thus provides an effective first layer of protection against EMI by shunting high frequency current directly to the device housing and away from internal circuitry where it can cause untoward effects as discussed above. Being physically located at the point where conductors enter the housing, the feedthrough filter may shunt current away from the conductors before they enter the housing thereby reducing the potential for high frequency energy to re-radiate from the conductors within the housing, possibly causing additional untoward effects. In general, the feedthrough filter must perform well and predictably over a wide range of potential EMI frequencies. Several feedthrough designs exist which accomplish these tasks and provide additional advantages as well; for example see U.S. Pat. No. 7,391,601. For convenience, the feedthrough filter circuit 110 and other similar capacitor circuits described herein may be referred to as feedthrough capacitors. It should be appreciated, however, that in some implementations such capacitors may not be implemented within a feedthrough, or that a feedthrough assembly may include elements other than capacitors.

As represented by the simplified representations of connectors 118 and 120, the implantable medical device may include a connector 118 that is configured to accept a connector 120 provided on a proximal end of the lead 104. In this way, the connectors 118 and 120 may enable signals to be coupled between the internal circuitry of the implantable medical device and an electrode (not shown) incorporated in the lead 104 (e.g., at a distal portion of the lead 104).

Figure 6:
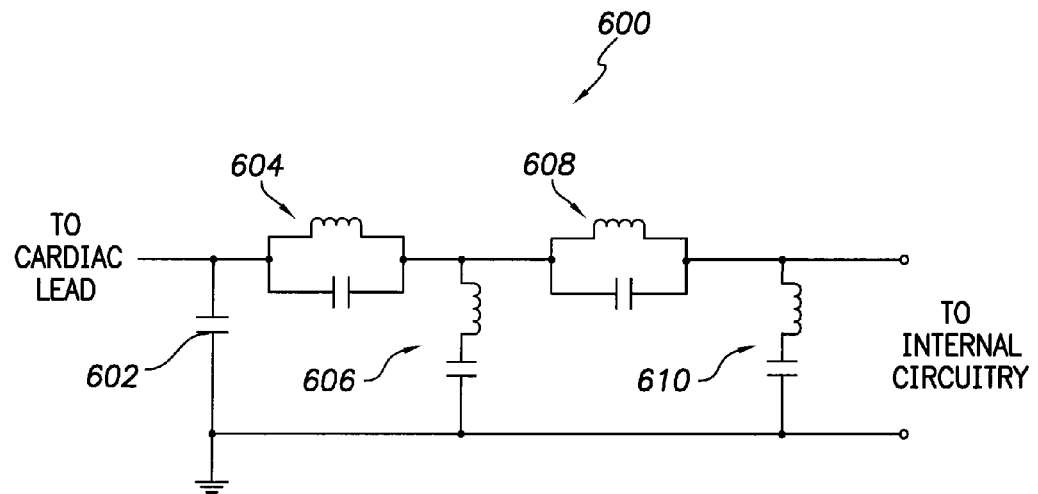
FIG. 6 is a simplified diagram of an embodiment of a high order filter consisting of a cascaded LC tank plus series LC filter circuit.
Figure 7:
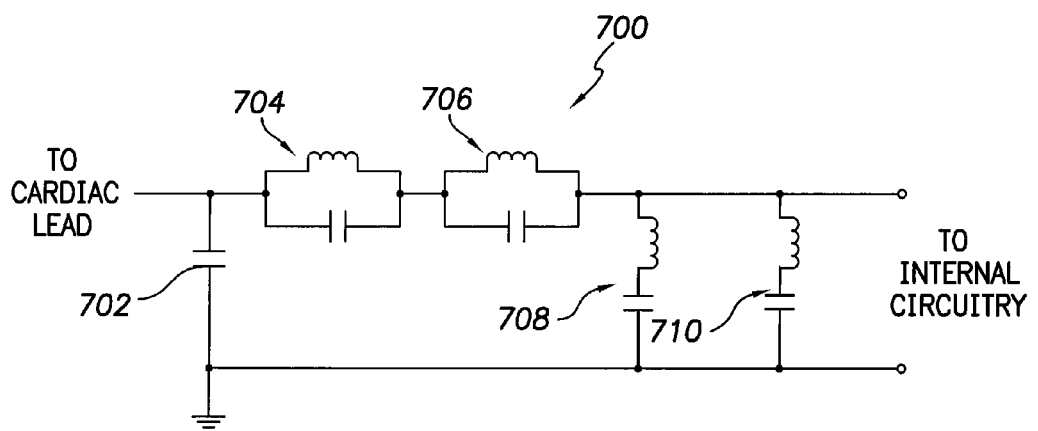
FIG. 7 is a simplified diagram of an embodiment of another configuration of high order LC tank circuits plus series LC filter circuits.

The filter circuit 102 employs a limited value for the total equivalent capacitance to reduce the amount of pulsed gradient-induced charge that may be imparted on a patient. For example, the total equivalent capacitance of a filter circuit may be on the order of 2.4 nanofarads or less. In the example of FIG. 1, the total equivalent capacitance may include the capacitance value of circuit 110 plus the capacitance value of circuit 114. In the examples of FIG. 6 and FIG. 7 discussed below, the total equivalent capacitance value may include the sum of the value of the feedthrough capacitor and the values of two capacitors in the two series LC circuits.

In addition, the LC tank circuit 112 and the shunt series LC circuit 114 are configured to attenuate MRI-induced RF energy and to compensate for any potential degradation in EMI protection that may be caused by the use of a low nominal capacitance value for the capacitor circuit 110. For example, the circuits 112 and 114 may be tuned (e.g., by defining their resonant frequencies) to remove signals in the range of approximately 64 MHz and/or 128 MHz.

As a specific example, in an implementation where the LC tank circuit 112 and the shunt series LC circuit 114 each have a resonant frequency of 64 MHz (e.g., the resonant frequency of the LC tank circuit 112 is substantially equal to (i.e., approximate) the resonant frequency of the shunt circuit 114), these circuits will significantly attenuate any MRI-induced signals in the range of 64 MHz. Specifically, around that frequency the LC tank circuit 112 will have high impedance that reduces MRI-induced current flow in the lead 104. In addition, the shunt series LC circuit 114 will have low impedance around that frequency that reduces the amount of RF signal voltage that may be coupled into internal circuitry of the implantable medical device. Here, it may be observed that the LC tank circuit 112 and the shunt series LC circuit 114 will effectively provide a voltage divider with respect to a voltage present at the lead 104. Since the impedance of the shunt series LC circuit 114 will be much less than the impedance of the LC tank circuit 112, a relatively small voltage will appear across the shunt series LC circuit 114 (and, correspondingly, the internal circuitry).

For convenience, FIG. 1 illustrates a single implantable cardiac lead coupled to internal circuitry of an implantable medical device. In practice, the filter circuit 102 or other similar filter circuitry (e.g., as taught herein) may be provided for multiple cardiac leads that are connected to an implantable medical device. For example, a separate filter network may be provided for each cardiac lead that connects to the device.

With the above in mind, several considerations that may be taken into account when designing a filter circuit as taught herein will be described with reference to FIGS. 2-4B. Briefly, FIGS. 2-3C illustrate how current may be induced within an implanted cardiac lead as a result of MRI scanning, and FIG. 4A is used to illustrate how these currents may be controlled to prevent unintended cardiac stimulation.

Figure 2:
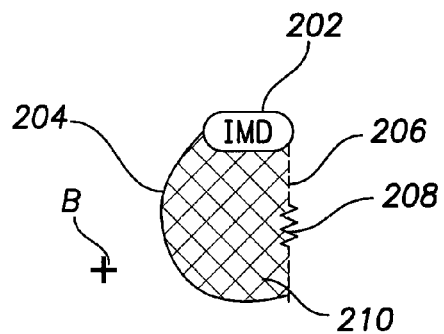
FIG. 2 is a simplified diagram of a theoretical loop area that illustrates how a MRI gradient may induce a signal in a cardiac lead.
Figure 3A:
FIGS. 3A-3B are simplified waveform diagrams associated with FIG. 2.
Figure 3B:
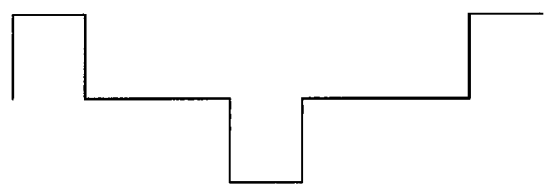
Figure 3C:
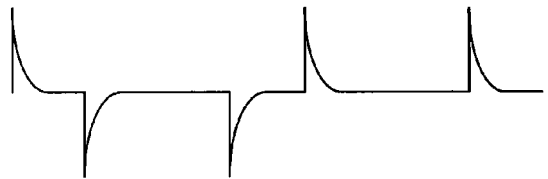
Figure 4A:
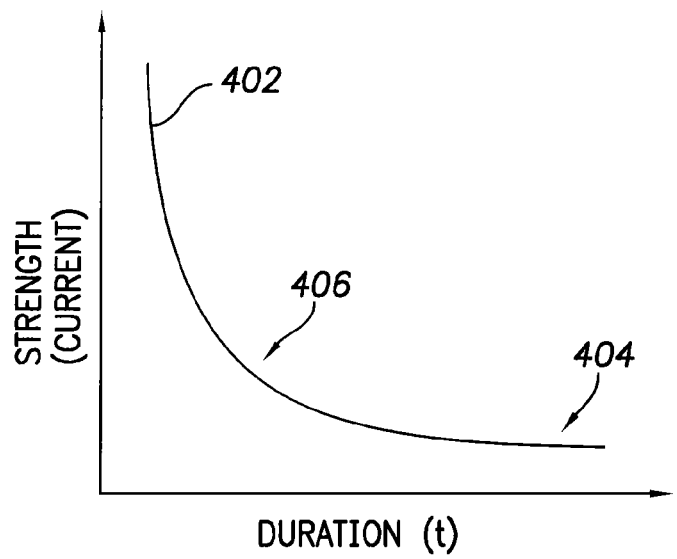
FIG. 4A is a simplified strength-duration curve.

FIGS. 2 and 3 illustrate a simple model how magnetic gradient pulses generated during MRI may induce voltage in an implanted cardiac lead, thereby causing current to flow through a filter circuit (e.g., a feedthrough capacitor) of an implantable medical device coupled to that lead. FIG. 2 represents a phantom filled with electrically conductive liquid, where B represents a magnetic flux density vector perpendicular to the page (e.g., the "+" symbol represents, in a simplified manner, a flux vector directed into the page). An implantable medical device (IMD) 202 and an associated cardiac lead 204 are illustrated with a loop area 210 (represented by the cross-hatched area) enclosed by the lead perpendicular to the vector B. The MRI scanning uses pulsed B fields (e.g., as represented by the idealized trapezoidal waveforms of FIG. 3A) to alter the magnetic field in a patient. This time varying B field induces voltages (e.g., as represented by FIG. 3B) proportional to the time rate of change of B and to the loop area (210). This voltage, in turn, induces current in the circuit containing the lead, the device and the conductive liquid. The current is controlled by the impedance of the circuit. For example, in an implantable medical device, the gradient induced voltage may mostly appear across the impedance of a feedthrough capacitor, giving rise to a current (e.g. as represented in FIG. 3C) proportional to the gradient induced voltage after high-pass filtering. In FIG. 2, the path of the induced current is illustrated in part by the dashed line 206 which is illustrated as returning from the lead 204 to the device 202 via the tissue of the patient (as represented by tissue impedance 208).

The induced currents described above have the potential to cause unintended cardiac stimulation. In some cases this unintended cardiac stimulation may induce cardiac fibrillation. Hence, it is desirable to increase the impedance of the illustrated path to attenuate the current spikes.

The duration of the current, and therefore also the amount of charge which may flow due to induction from pulsed magnetic fields in an implantable medical device, may be reduced by using smaller feedthrough capacitors (i.e., by using a capacitor with a smaller nominal capacitance value). For example, if the only path for charge (Q) is through the feedthrough capacitor, the reduction in charge is proportional to the reduction in capacitance (C) for a voltage step of magnitude V according to the relationship $Q=CV$.

Figure 4B:
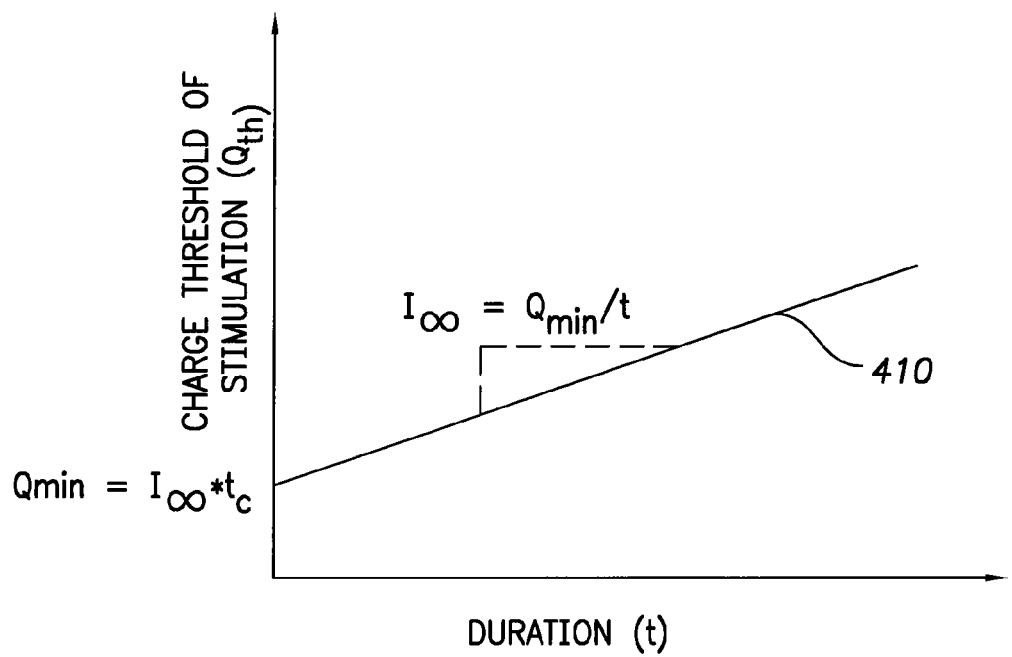
FIG. 4B is a simplified charge threshold versus duration curve.

FIGS. 4A and 4B depict, respectively, a strength duration curve 402 that relates the duration of a pulse to the pulse intensity that may cause stimulation of cardiac tissue and a plot 410 of threshold in terms of charge. The curve 402 may be used to determine how much MRI-induced current a patient may tolerate. In particular, the curve 402 illustrates that as the duration of the pulse decreases, the intensity must increase hyperbolically in order to stimulate the cardiac tissue. Here, the Rheobase 404 is the stimulus intensity at infinite duration. The Chronaxie 406 is the stimulation duration at twice the Rheobase.

An example of the amount of charge that may induce stimulation of cardiac tissue follows. The Chronaxie for human heart tissue has been determined to be on the order of 0.5 milliseconds. A Rheobase may be chosen as 10 microamps or 50 microamps as a sample worst-case scenario. Based on the above, a minimum charge to cause cardiac tissue to stimulate may be calculated as set forth in Equations 1-3:

$$\text{Current} = b\left(1 + \frac{c}{d}\right) \qquad \text{EQUATION 1}$$

$$\text{Charge} = b\left(1 + \frac{c}{d}\right) \cdot d \qquad \text{EQUATION 2}$$

$$\text{Charge}_{minimum} = c \cdot b \qquad \text{EQUATION 3}$$

Where b is the rheobase, c is the chronaxie and d is pulse duration.

For pulse durations much smaller than Chronaxie, the charge reaches an asymptote of Rheobase times Chronaxie. As a result, the stimulation should be less than approximately 25 nanocoulombs to avoid stimulation in this example.

Using the value of 25 nanocoulombs and a maximum induced voltage of 7.5 volts (e.g., assuming a dB/dt of 200 Teslas per second and a 377 square centimeter loop area, as specified by the EMC standard for medical devices: ANSI/AAMI PC69 2nd ed.), a capacitance of 3.3 nanofarads is obtained, depending on the Rheobase, per the relationship C=Q/V. Thus, the use of a feedthrough capacitor (or total equivalent capacitance of a filter circuit) of less that 3.3 nanofarads may ensure that no stimulation will occur because the width of the current pulse will be too short. Again, this calculation is based on the assumption that the induced voltage does not exceed the above maximum value (e.g., which may be determined based on maximum MRI scanning parameters such as maximum scanning power and slew rates). Additionally, note that this simple example assumes that the only path for charge is through the feedthrough capacitor. In practice, there may be additional paths for charge flow which must be considered, e.g., through elements of the filter circuitry taught herein.

With the use of a smaller feedthrough capacitor, the implantable medical device may be more susceptible to external EMI (e.g., from cell phones or other interfering RF sources). Likely the strongest source of EMI an implantable device may be exposed to is an MRI scanner. As mentioned above, however, the filter circuitry taught herein (e.g., the LC tank and shunt series LC combination) may be employed to attenuate any EMI frequencies that are not sufficiently attenuated by the feedthrough capacitor, in particular those frequencies associated with MRI.

From an overall systems point of view, several factors may be considered relating to the performance of the filter circuitry. For example, preferably the filter will have deep attenuation for both RF current and voltage in order to attenuate EMI as much as possible, particularly at frequencies associated with MRI where the largest amplitude EMI signals are expected to be found. In addition, the filter will preferably have a relatively wide bandwidth to allow for increased tolerance of the components, reduce component cost, and increase manufacturability and reliability.

Additionally, the filter must not appreciably interfere with the intended function of the device, which for example, may involve sensing bioelectric signals and electrically stimulating excitable tissue. Therefore the filter must not attenuate appreciably at frequencies associated with relevant bioelectric and stimulation signals. The filter design should accommodate the presence of a feedthrough capacitor as applicable, ideally allowing the feedthrough capacitor's design value to be varied without interaction, and not degrading the feedthrough capacitor's ability to provide attenuation over the widest possible range of potential EMI frequencies. The filter should present a minimum equivalent capacitance in parallel with the feedthrough capacitor, as the total equivalent capacitance of the filter and feedthrough capacitor together will determine the charge that flows in response to induced voltage in the lead and therefore must be kept small; while at the same time, the feedthrough capacitor value should be kept as large as possible to provide maximum broadband attenuation. The filter should be tolerant of changes in impedance between its connections to the device's internal circuitry; as such changes are likely to occur with time as part of the device's normal operation. The filter should be tolerant of impedance variation in an attached lead, as this may vary from lead to lead and from implant to implant.

In practice, the internal circuitry for each channel (e.g., a Tip or Ring circuit) of an implantable medical device may be different. Consequently, the input impedance of each channel also may be different. Moreover, a given channel's input impedance may change with a change in the output signal of the channel. As a result of these complicated impedance differences and impedance changes, it is desirable for a filter to have both low impedance to the input or output circuits of the implantable medical device and low impedance to the lead side (via the feed thru capacitor) to reduce the coupling effect with the lead while blocking the high RF current from the lead. For example, by using a 1.5 nanofarad feedthrough capacitor, at a frequency of 64 MHz the filter may have an impedance of approximately 1.5 ohms at the lead side. Consequently, the filter may not cause appreciable coupling effect even if the impedance of a lead varies significantly (e.g., 50-700 ohms) due to, for example, changes in the orientation of the lead or other factors. For the implantable medical device side of the filter, while the sensing circuitry of the implantable medical device may have a relatively high impedance, the pacing circuitry of the implantable medical device may have a relatively low impedance during pacing operations (e.g., when the pacing capacitor is charging). Hence, it is desirable to also have low filter impedance at the implantable medical device side to reduce loading. In accordance with the teachings herein, this may be accomplished through the use of a shunt series LC circuit which may have low impedance (e.g., on the order of 500 milliohms or less) at the resonant frequency.

Various types of lumped filters may be used to attenuate RF energy at MRI frequencies. For example, as described above an LC lumped filter may be employed. There are two fundamental LC tuning circuits: an LC tank circuit (e.g., filter 112) and a series LC circuit (e.g., filter 114). These filters may be tuned to a particular frequency (a resonant frequency) as described in Equation 4:

$$f = \frac{1}{2\pi\sqrt{LC}} \qquad \text{EQUATION 4}$$

As mentioned above, the attenuation performance of these filters may be specified by selecting a particular resonant frequency. Specifically, the LC tank filter will have maximum impedance at its resonant frequency, while the series LC circuit will have minimum impedance at its frequency. Based on the signals expected to be induced by MRI scanning, an LC tank circuit, a series LC circuit, or some combination of these filter circuits may be employed to attenuate the induced signals.

In a filter system employing multiple tuned circuits, the tuned circuits may be tuned to the same frequency or different frequencies. For example, in some implementations the circuits 112 and 114 may both be tuned to the same frequency (e.g., 64 MHz or 128 MHz). In other implementations the circuits 112 and 114 may be tuned to different frequencies. As a specific example, the circuit 112 may be tuned to 64 MHz while the circuit 114 is tuned to 128 MHz. As another example, the circuit 112 may be tuned to 128 MHz while the circuit 114 is tuned to 64 MHz.

In some aspects the selected frequency is based on one or more frequencies associated with MRI scanning. For example, MRI scanning at 1.5 Tesla may induce signals having a frequency on the order of 64 MHz, while MRI scanning at 3.0 Tesla may induce signals having a frequency on the order of 128 MHz. Accordingly, a filtering system may be designed to attenuate either one or both of these signals.

Figure 5:
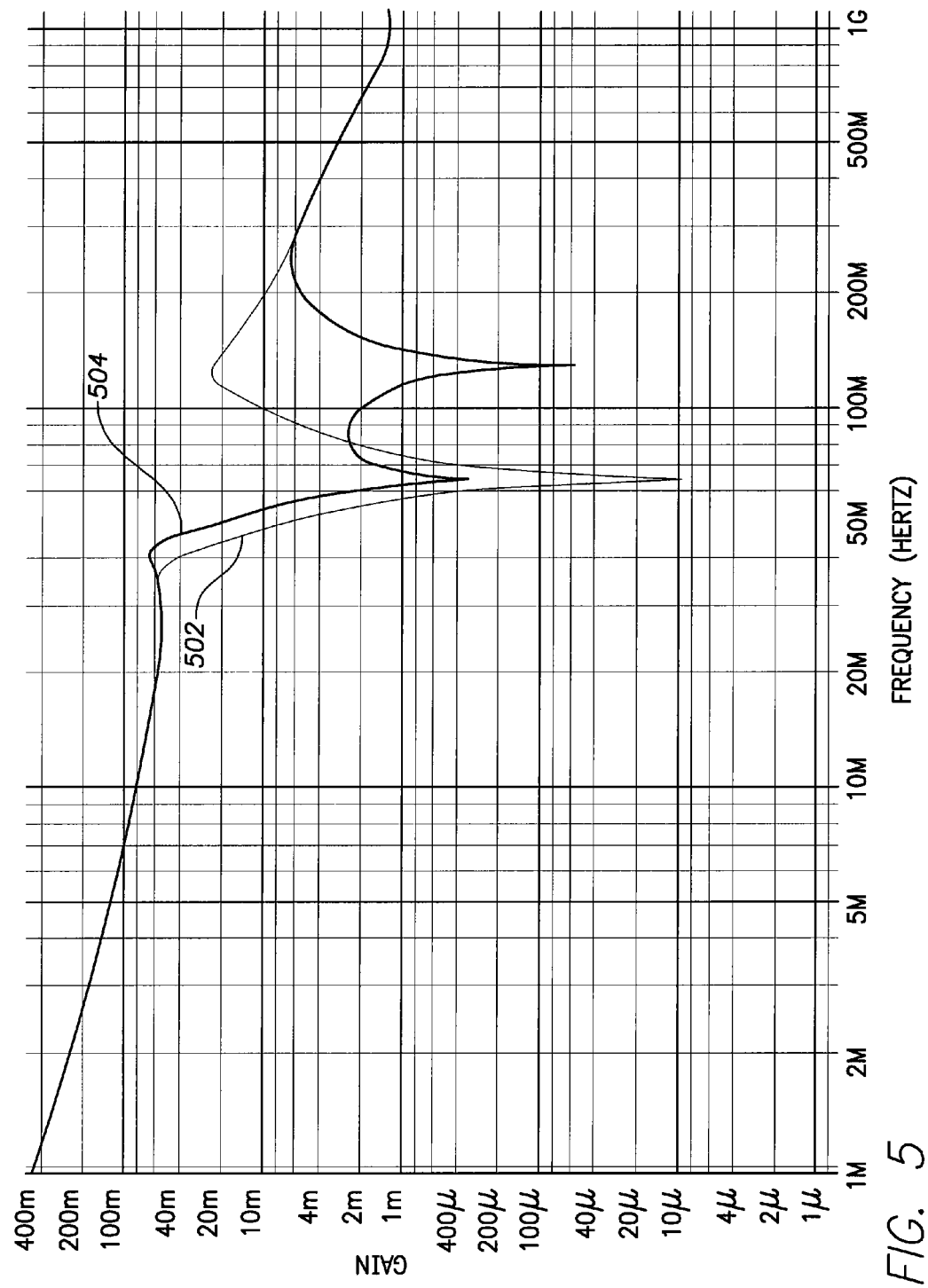
FIG. 5 depicts simplified frequency response curves for different filter embodiments from FIG. 1.

FIG. 5 illustrates sample attenuation curves for a single frequency band stop filter (curve 502) and a double frequency band stop filter (curve 504). In the example of FIG. 1, curve 502 may relate to a 64 MHz resonant frequency for the circuits 112 and 114, and a value of 1.2 nanofarads for the capacitor circuit 110. Conversely, curve 504 may relate to a 64 MHz resonant frequency for the circuit 112, a 128 MHz resonant frequency for the circuit 114, and a value of 1.2 nanofarads for the capacitor circuit 110.

Due to superimposition and inter-coupling effects of these topologies, the resulting band stop filters may have a wider and deeper attenuation curve than other types of filters. As shown by curve 504, when the LC tank and series LC circuits are tuned at different resonant frequencies and work together with the feedthrough capacitor, the super-imposition and inter-coupling effect may generate a relatively wide and deep filter curve. In addition, when the LC tank and series LC circuits are tuned at the same resonant frequency and work together with the feedthrough capacitor, the super-imposition and inter-coupling effect also will generate a wide and deep filter curve. In this later case, the total attenuation may be more than double the attenuation provided by the dual frequency shunted series LC filter topology.

The super-imposition and inter-coupling effect play a key role in this particular LC tank plus series LC topology. There are four parts of the circuit that will cause these superimposition and inter-coupling effects: 1) the LC tank in the signal chain; 2) the series LC circuit connected between the signal chain and ground; 3) the feedthrough capacitor; and 4) the lead equivalent circuit (although very small, still has coupling effect).

As illustrated in FIG. 1 above, implantable medical devices such as implantable pulse generators (e.g., pacemakers) may have one or more internal circuits that are coupled to an implantable cardiac lead. For example, a device may include a pacing circuit that generates pacing pulses to be applied via the lead and a sensing circuit that senses cardiac signals via the lead. Typically, these circuits are configured in parallel across a pair of electrodes (e.g., an electrode of the lead and a case electrode).

To maintain the integrity of the internal circuits, any impedance added in series to the cardiac lead (e.g., resistor 908 in FIG. 9) should not be too large. In particular, lead impedance should not be increased during the pacing pulse since this may increase the capture threshold. If the capture threshold increases too much, capture may not be possible. Also, an increase in the capture threshold may necessitate multiplication of the battery voltage by the charge pump (e.g., part of pulse generator 1622 and/or pulse generator 1624 in FIG. 16). In this case, the longevity of the implantable device may decrease significantly.

In practice, sensing is less likely to be affected by any added series impedance since the input impedance of the sense amplifier may be very high (e.g., on the order of 100 k ohms). However, induced current and/or RF energy traveling from the cardiac lead through the tissue of the patient to the implantable medical device (e.g., as shown in FIG. 2), may result in noise that may be detected by the sense amplifier. Accordingly, sensing may be disabled during MRI scanning. For example, the implantable medical device may be programmable whereby an attending physician may send a command (e.g., via telemetry) to the device (e.g., an MRI controller in the device such as MRI controller 1639 shown in FIG. 16) to temporarily turn off sensing. Alternatively, the implantable medical device may include an MRI controller (e.g., MRI controller 1639 comprising one or more MRI detectors) that automatically detects the presence of MRI signals (e.g., in one or more axes). In this case, the implantable medical device may automatically disable sensing when an MRI signal is detected, and re-enable sensing when the MRI signal is no longer detected.

Figure 8:
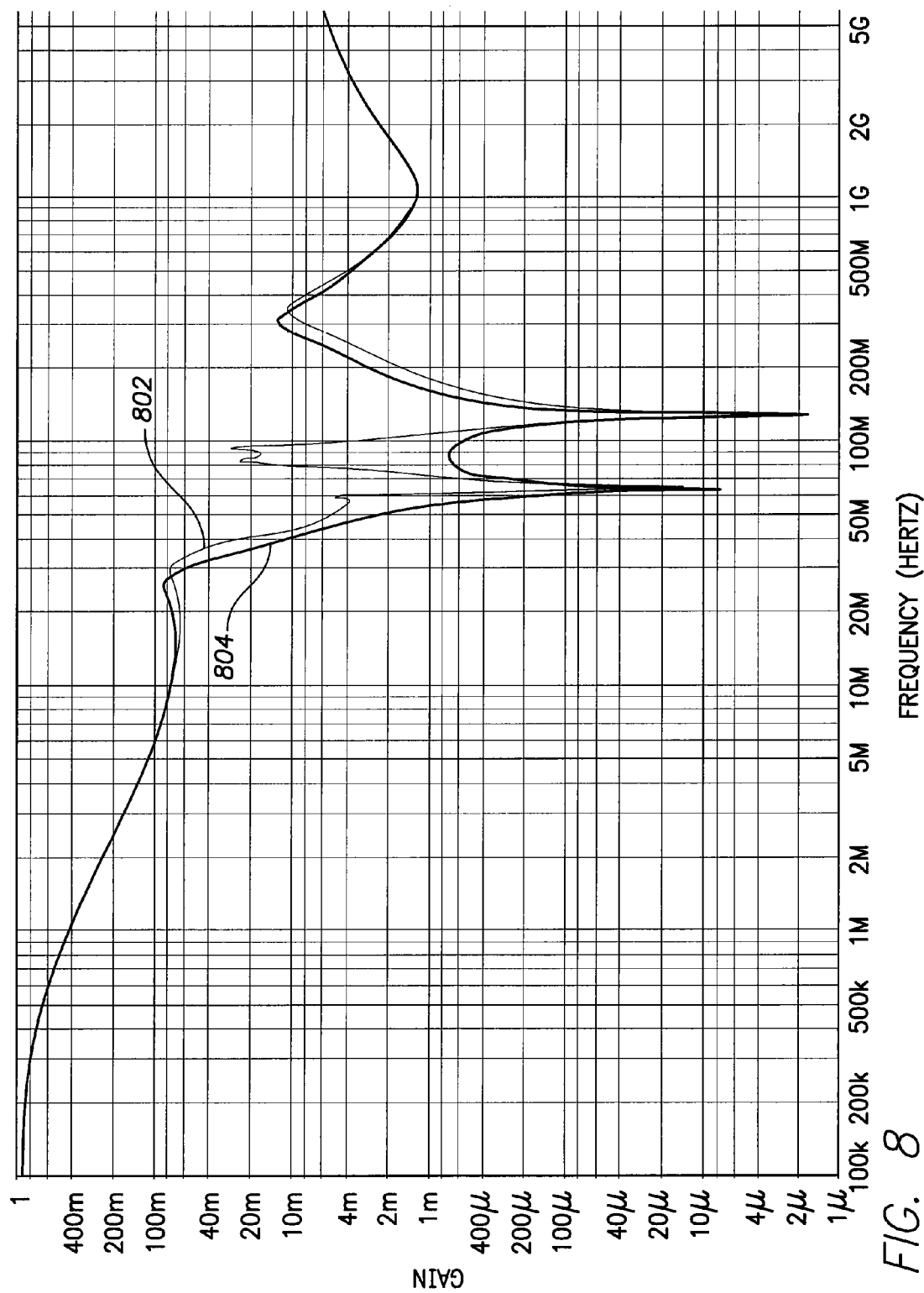
FIG. 8 depicts simplified frequency response curves for the high order LC tank plus series LC filter circuits embodiments for FIG. 6 and FIG. 7.

Referring now to FIGS. 6-8, examples of filter systems that employ multiple tuned circuits are described. FIG. 6 illustrates an implementation that employs two sets of parallel and series LC circuits. Specifically, a filter circuit 600 includes a feedthrough capacitor 602, a first LC tank circuit 604, a first shunt series LC circuit 606, a second LC tank circuit 608, and a second shunt series LC circuit 610. FIG. 7 illustrates an implementation that employs a set of two LC tank circuits and a set of two series LC circuits. Here, a filter circuit 700 includes a feedthrough capacitor 702, a first LC tank circuit 704, a second LC tank circuit 706, a first shunt series LC circuit 708, and a second shunt series LC circuit 710.

In some implementations the tuned circuits may be configured to attenuate different frequencies. For example, in FIG. 6 the circuits 604 and 606 may each have a resonant frequency of 64 MHz, while the circuits 608 and 610 may each have a resonant frequency of 128 MHz. In FIG. 7 the circuits 704 and 708 may each have a resonant frequency of 64 MHz, while the circuits 706 and 710 may each have a resonant frequency of 128 MHz.

FIG. 8 illustrates a sample attenuation curve (curve 802) for the filter circuit 600 and a sample attenuation curve (curve 804) for the filter circuit 700. Both filter systems have the super-imposition and inter-coupling effect, and have more than twice the attenuation as compared to the filter systems shown in FIG. 9. However, the filter circuits 600 and 700 have different overshoot and bandwidth performance.

Figure 9:
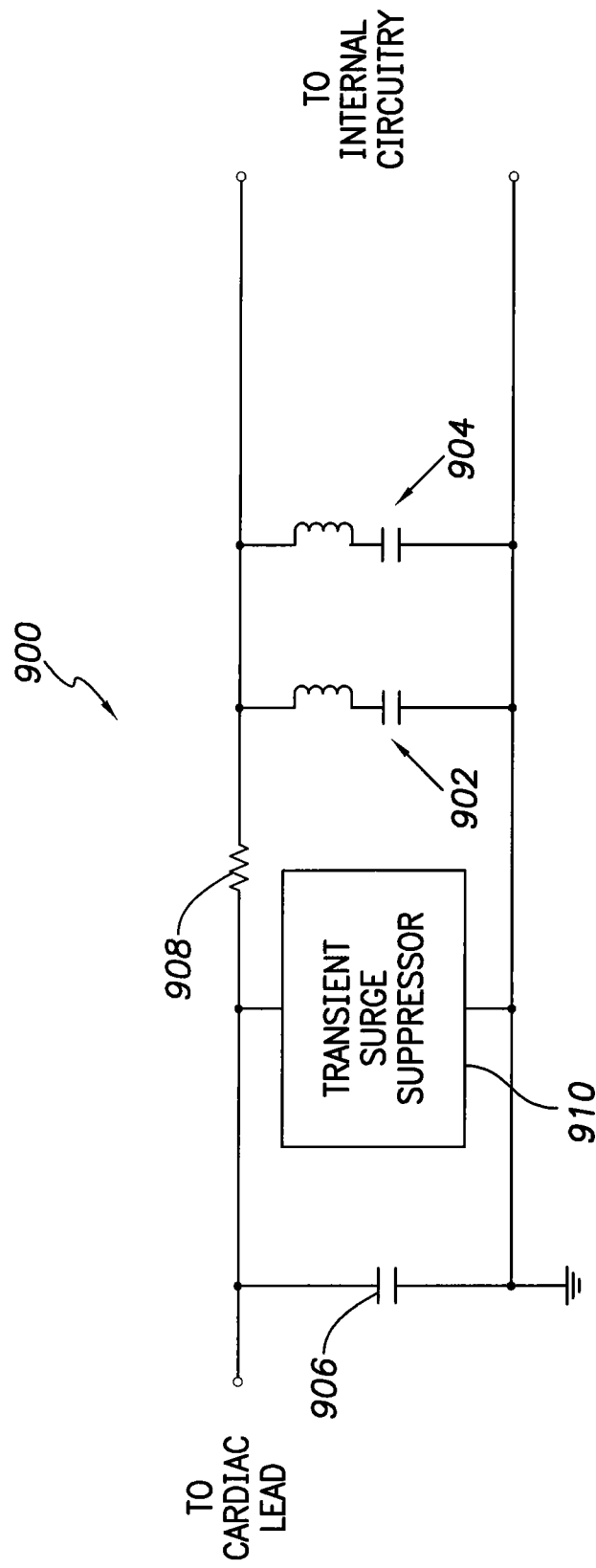
FIG. 9 is a simplified diagram of an embodiment of a circuit (shunt series LC filters) that filters MRI-induced signals for an implantable medical device.

FIG. 9 illustrates a filter circuit 900 that employs two sets of shunted series LC circuits 902 and 904. Here, the circuits 902 and 904 may be tuned to different frequencies (e.g., 64 MHz and 128 MHz) to remove induced RF energy associated with these frequencies and to compensate for any potential degradation in EMI protection that may be caused by the use of a smaller feedthrough capacitor 906.

In some implementations a resistor 908 may be employed in series with the cardiac lead (e.g., if the inherent resistance in the signal chain does not sufficiently isolate the series LC circuits from the feedthrough capacitor, thereby resulting in overshoots). Here, the resistance inherent in the signal chain may comprise, for example, printed circuit board trace resistance and impedance and inductor coil resistance (e.g., either of which may relate to skin effect at RF frequencies). In cases where a relatively small resistor (e.g., on the order of 10 ohms) is used here, a transient surge suppressor 910 (e.g., an external defibrillation protection network) may be employed on the cardiac lead side of the resistor 908 to protect the resistor 908 from being damaged by relatively large voltage surges (e.g., which may be generated if defibrillation shocks are applied to a patient). Here, the transient surge suppressor (TSS) 910 may be placed immediately after the feedthrough if the peak expected induced voltage (e.g., 7.5 volts) is not sufficient to activate the transient surge suppressor 910.

Figure 10:
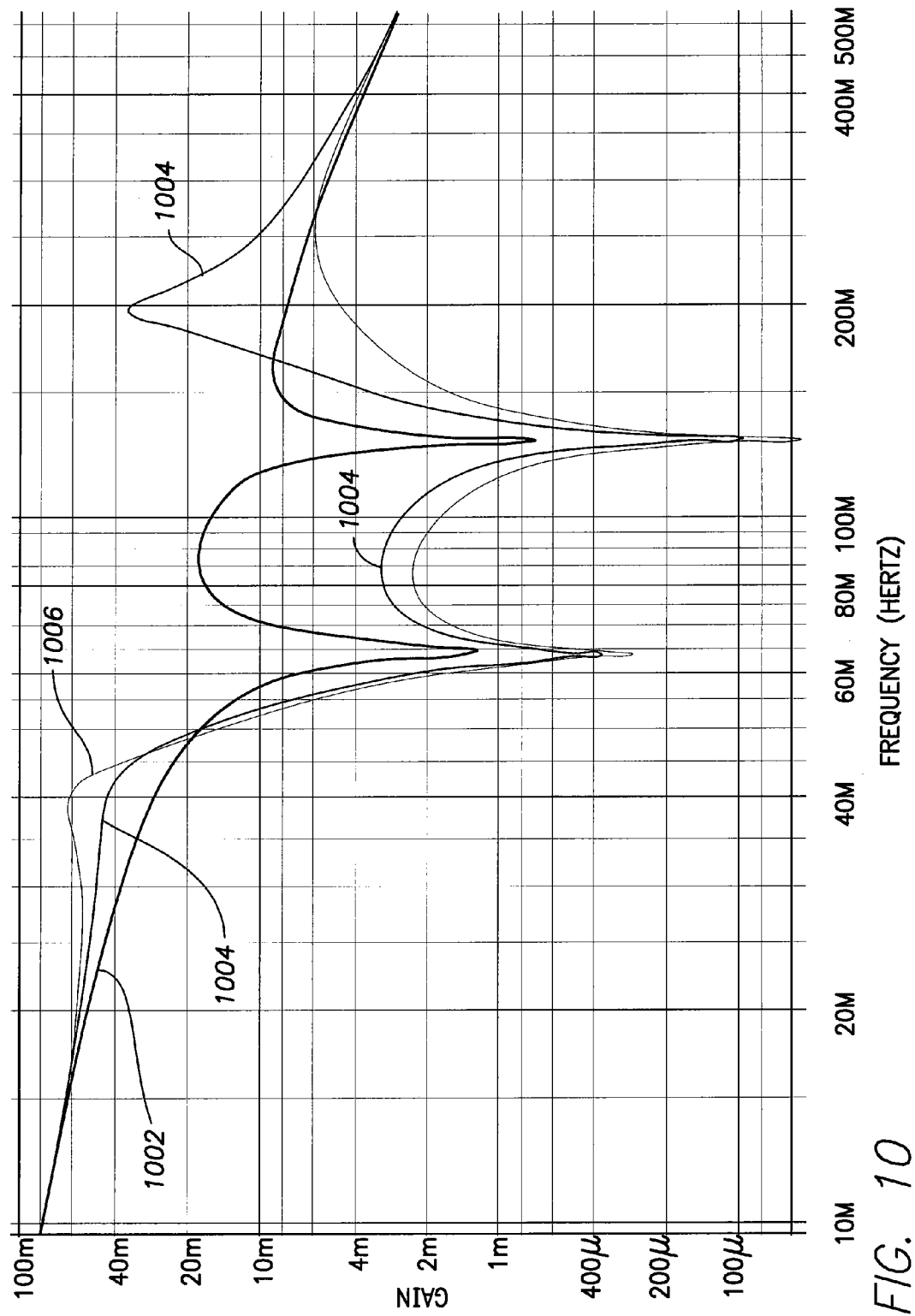
FIG. 10 depicts simplified frequency response curve comparison between LC tank plus series LC filter and shunt series LC filters.

FIG. 10 illustrates sample attenuation curves that compare the filter circuit 900 (curve 1002) with different implementations of the filter circuit 102 (curves 1004 and 1006). Specifically, curve 1002 corresponds to filter circuit 900 where the feedthrough capacitor 906 is 1.2 nanofarads, the resistor 908 is 6 ohms, the resonant frequency of the circuit 902 is 64 MHz, and the resonant frequency of the circuit 904 is 128 MHz. Curve 1004 corresponds to filter circuit 102 where the feedthrough capacitor 110 is 1.2 nanofarads, the resonant frequency of the circuit 112 is 128 MHz, and the resonant frequency of the circuit 114 is 64 MHz. Curve 1006 corresponds to filter circuit 102 where the feedthrough capacitor 110 is 1.2 nanofarads, the resonant frequency of the circuit 112 is 64 MHz and the resonant frequency of the circuit 114 is 128 MHz.

From FIG. 10 it may be seen that both implementations of the filter circuit 102 have a wider bandwidth and deeper attenuation than the filter circuit 900. Accordingly, a filter may be constructed using less expensive components (e.g., capacitors and inductors) that have lower tolerance (e.g., +/−2% as opposed to +/−0.5%) while still providing effective attenuation at the desired frequencies (e.g., 64 MHz and 128 MHz). In other words, even though the resonant frequencies of the filter may not be precisely 64 MHz and 128 MHz due to the lower tolerance of these components, the filter will still provide adequate filtering at 64 MHz and 128 MHz due to the wider bandwidth and deeper attenuation of the filter. A sample design method for the circuit 102 follows.

The LC tank and shunt series LC tuning frequencies can be calculated by Equation 4 set forth above. Once the center frequency is determined, the product value for the L×C can be calculated. For example, the capacitor value 100 picofarads may be arbitrarily selected. It is noted that a small capacitor value is desirable so as to keep small the equivalent capacitance which the filter will place in parallel with the feedthrough capacitor. Then, at 64 MHz, either the parallel or series LC circuit have the product value 59.4 nanohenries× 100 picofarads=5940×10$^{-21}$. As another example, if the randomly selected capacitor value is 300 picofarads, at 128 MHz either the parallel or series LC circuit have the product value 5.1 nanohenries×300 picofarads=1530×10$^{-21}$. It should be noted that the inductor in the LC tank (e.g., tank 112) may need to carry significant current in the event of external defibrillation of the patient, because a TSS as previously described may be part of the cardiac stimulation circuit 106. Therefore, a low value for the inductor of the LC tank 112 may be desired. This is because a low value inductor may be realized by fewer turns of wire and/or larger gauge wire, and therefore may have lower resistance and higher current carrying capability compared to a larger value inductor of similar physical size. This will necessitate that the parallel capacitor forming the LC tank 112 to increase proportionally in order to achieve the desired resonant frequency. This is in opposition to the desire that the equivalent capacitance which the filter 102 places in parallel with the feedthrough capacitor 110 be kept small. However the problem may be mitigated by choosing the capacitor of series LC circuit 114 to be as small as possible, since the overall equivalent capacitance of the filter 102 must be less than either capacitor according to the relationship $C_{equiv}=C_{110}+C_{114}$.

In the next step, simulation tools may be used to determine the width and attenuation level of the attenuation curve by combining different sets of the values for L and C. Based on simulation optimizations several conclusions may be made here (the variable L value may be used to determine the filter performance).

For circuit 112, values from 5.1 nanohenries to 33 nanohenries (e.g., 5.1 nH, 10 nH, 15 nH, 22 nH, 30 nH and 33 nH) are selected. Increasing the value of the inductance for circuit 112 from 5.1 nH will cause a wider attenuation curve and deeper attenuation. If the value of the inductance for circuit 112 is increased above 33 nH, the previous effect is no longer dominant.

For circuit 114, values from 3.1 nanohenries to 33 nanohenries (e.g., 3.1 nH, 5.1 nH, 12.5 nH, 20 nH, and 33 nH) are selected. In some implementations increasing the value of the inductance for circuit 114 from 5.1 nH to 12.5 nH may greatly increase the overshooting (or positive peak) at the left stop band. Also it may narrow the bandwidth. In circuit 114, a large inductance value also may increase the overshooting (or positive peak) at the two borders of the filter attenuation curve.

From FIG. 10, it may be observed that when using a 64 MHz tuning frequency for the LC tank circuit (curve 1006), an overshoot (or positive peak) is generated at the left of the stop band. When using a 128 MHz tuning frequency for the LC tank circuit (curve 1004), an overshoot (or positive peak) is generated at the right border of the curve.

Figure 11:
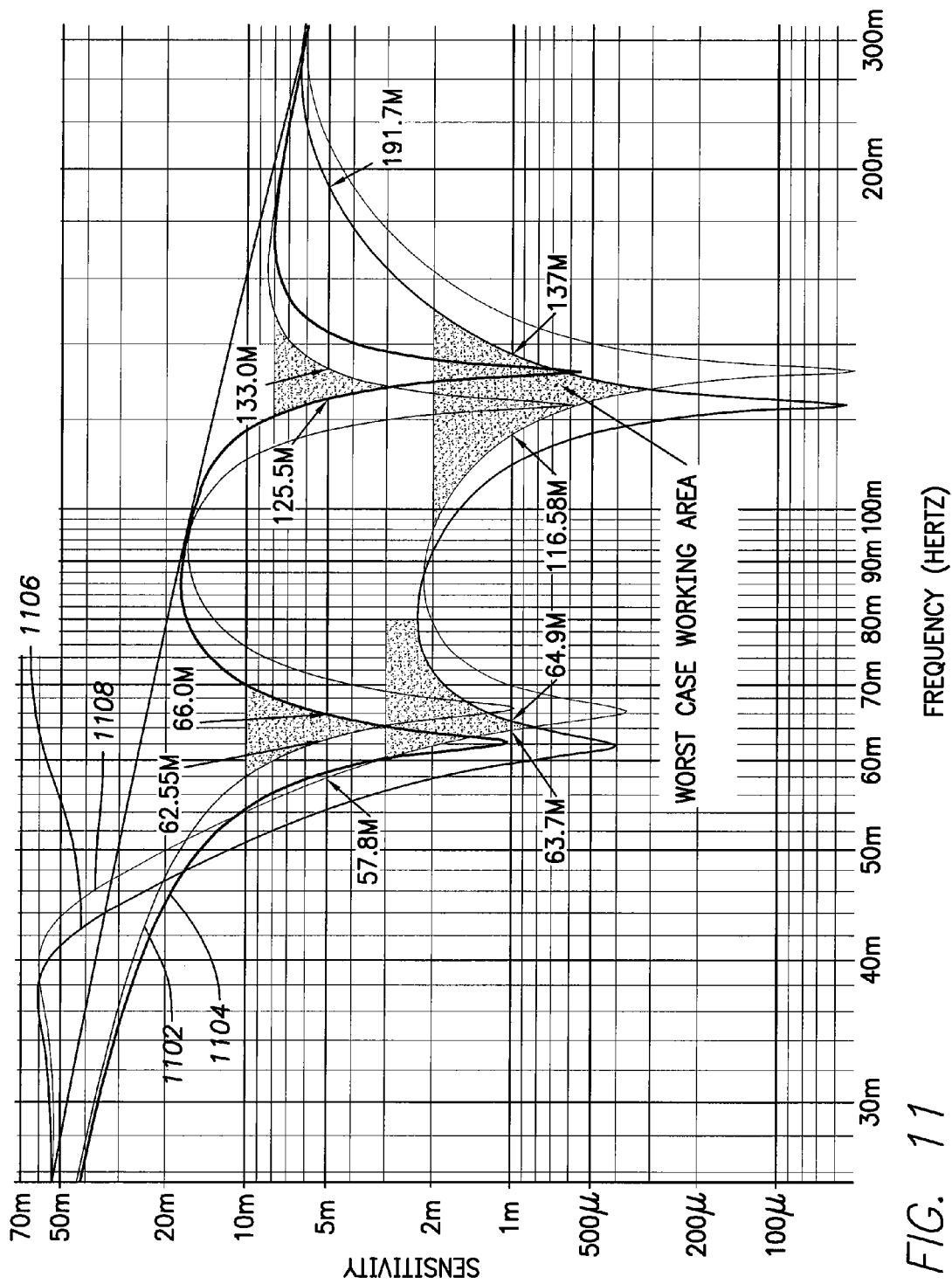
FIG. 11 depicts simplified sensitivity curve comparison between LC tank plus series LC filter and shunt series LC filters.

FIG. 11 illustrates a sample component sensitivity analysis for the filter circuit 102 (curves 1106 and 1108) and the filter circuit 900 (curves 1102 and 1104). For inductors with +/−2% tolerance and capacitors with +/−5% tolerance, FIG. 11 illustrates that the filter circuit 102 has a much deeper and wider working area (e.g., as represented by the shaded areas) than the filter circuit 900 (e.g., as a result of the wider bandwidth and deeper attenuation of the filter circuit 102). Thus, the filter may be constructed using less expensive components that have lower tolerance (e.g., +/−2%-5% as opposed to +/−0.5%) while still providing good performance at the desired frequencies (e.g., 64 MHz and 128 MHz). Consequently, the filter circuit 102 may be more reliable, more manufacturable, and have lower component cost.

It should be appreciated that, in practice, the capacitors and inductors discussed herein are more precisely characterized by RF capacitor and inductor equivalent models. In these models, the capacitor and inductor will have their own series resonant frequency (SRF). A capacitor operating in an RF band functions primarily as a capacitor below its SRF frequency, and more as an inductor above its SRF frequency. A similar but inverse principle applies for an inductor.

Taking the capacitor and inductor equivalent models into account, preferably the capacitor and inductor will have a very high SRF and Q (quality factor), at least 4-6 times higher than the filter's center frequency. Both the capacitor and inductor preferably have very low ESR (equivalent series resistance) value. High ESR value of the inductor and capacitor will reduce the attenuation level and the overshooting.

Figure 12:
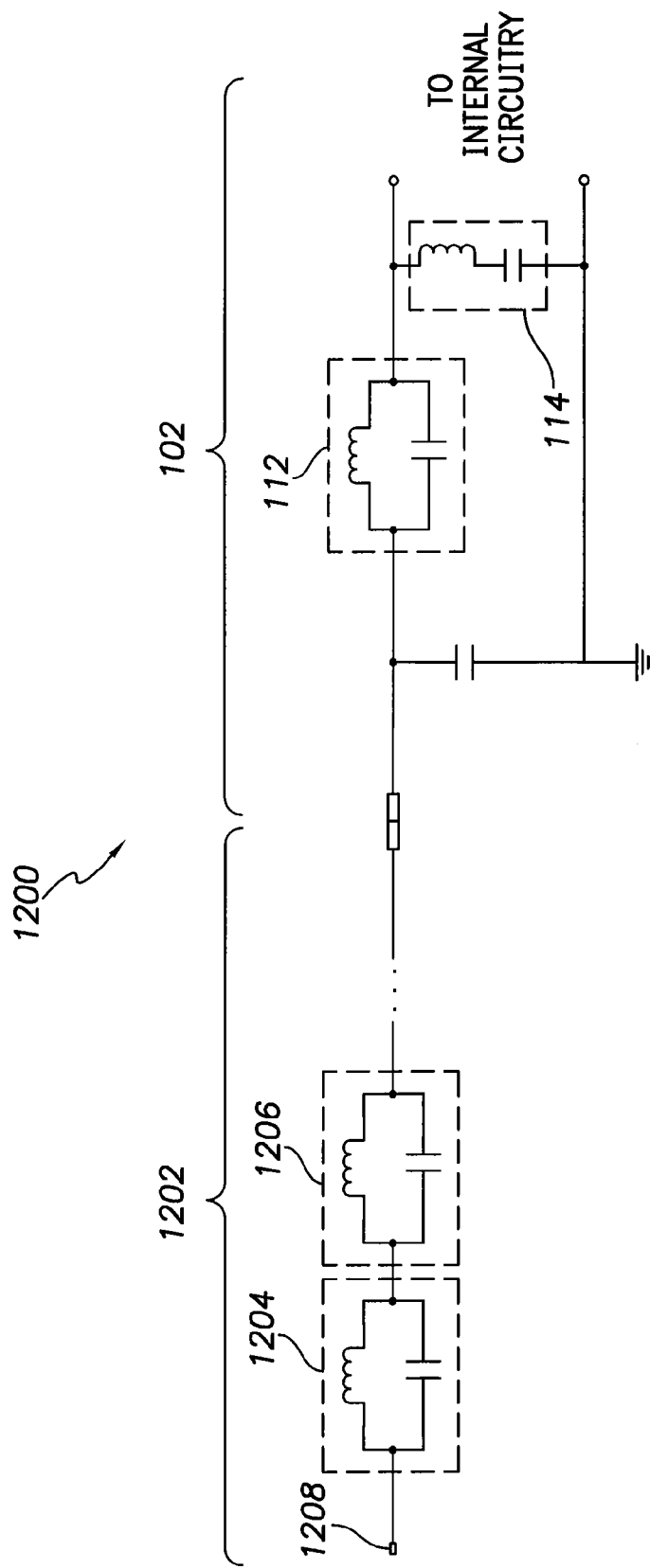
FIG. 12 is a simplified diagram of an embodiment of an implantable medical system that filters MRI-induced signals through the use of a filter circuit in an implantable cardiac lead.

As mentioned above, in some implementations an implantable cardiac lead includes a filter circuit to attenuate MRI-induced current flow in the lead. FIG. 12 illustrates an example of an implantable medical system 1200 where an RF current limiting filter in a cardiac lead 1202 operates in conjunction with the filter circuit 102 to mitigate MRI-induced signals. Two LC tank circuits 1204 and 1206 are implemented at a distal portion of the lead 1202 to limit MRI current at their corresponding resonant frequencies (e.g., 64 MHz and 128 MHz). Due to the high impedance (e.g., above 1000 ohms at the center frequency) of each LC tank circuit, these circuits significantly limit the current flow in the distal portion of the lead associated with any induced RF signals that have frequencies at or near the resonant frequencies.

In addition, the low impedance of the interface between the head of the lead (e.g., a distal tip electrode 1208) and cardiac tissue, and the high impedance across the circuits 1204 and 1206 function as a voltage divider to eliminate most RF voltage at the interface between cardiac tissue and the lead head, thus mitigating the potential hazard of heating at the tip-tissue interface due to MRI.

Furthermore, as discussed above, the filter circuit 102 will limit RF current from the lead 1202 by reducing the RF voltage at the input side of the internal circuitry (not shown) of the implantable medical device by operation of the voltage dividing effect of the high impedance of LC tank circuit 112 and the low impedance of the shunt series LC circuit 114. Hence, the filtering system of FIG. 12 may effectively mitigate the effects of any induced RF current and voltage in the system 1200.

In some implementations it may be desirable to provide more attenuation than may be efficiently achieved through the use of passive circuits as described above. In such a case, an active switching network may be used in an attempt to prevent induced signals from entering internal circuitry of an implantable medical device.

Figure 13:
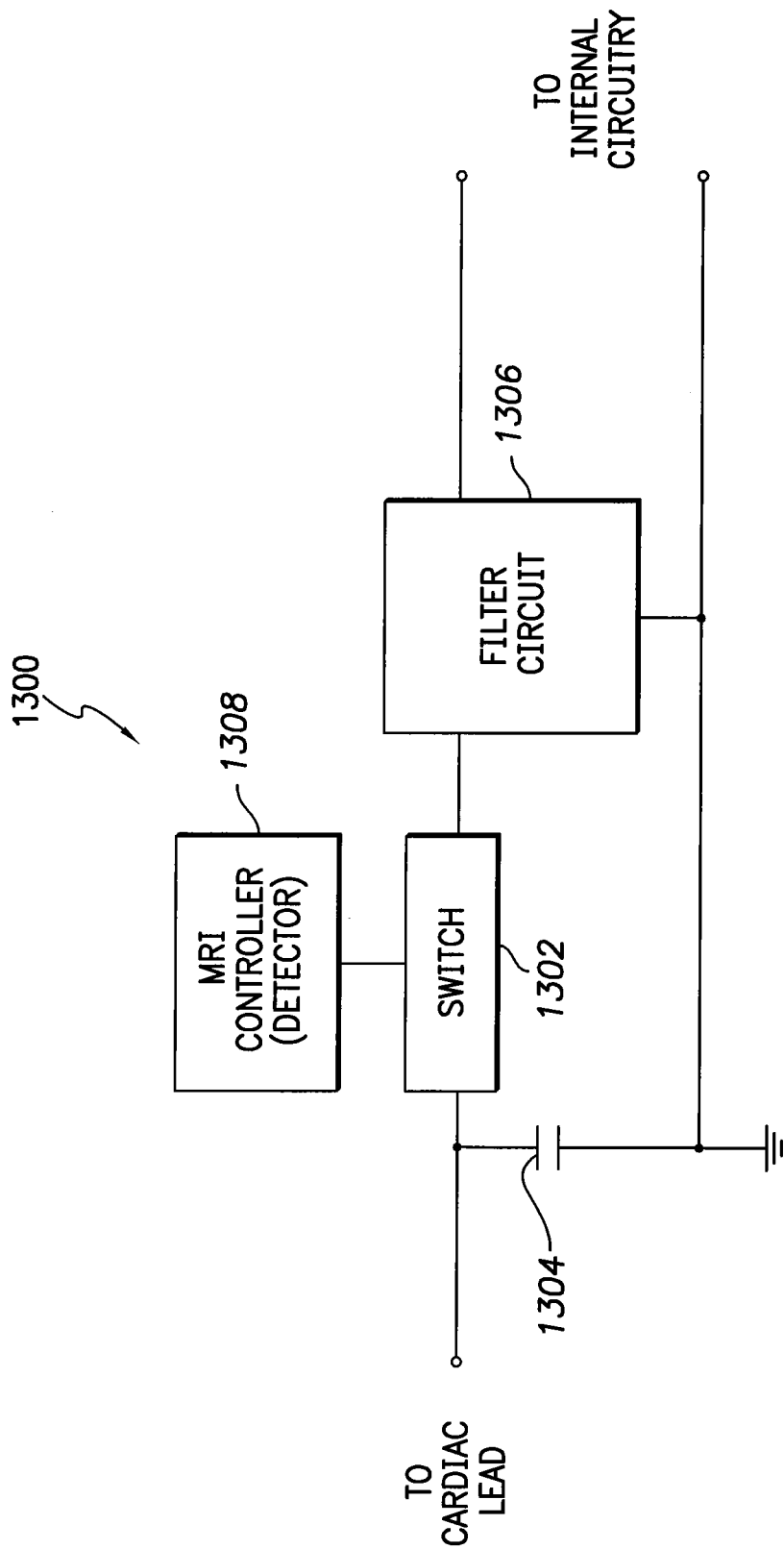
FIG. 13 is a simplified diagram of an embodiment of an active switching network that may provide protection for an implantable medical device (e.g., high voltage protection for a shunt series LC filter)

FIG. 13 illustrates a simplified example of a circuit 1300 employing an active switch 1302 (e.g., a field-effect transistor) placed in series with a cardiac lead (not shown). The switch 1302 may be open to block induced current when the implantable medical device is subjected to MRI. Such a switch may be used instead of or in combination with a feedthrough capacitor and a filter circuit as taught herein. For example, the circuit 1300 may include a feedthrough capacitor 1304 and/or a filter circuit 1306 (e.g., implementing an embodiment as described in FIG. 1, FIG. 6, FIG. 7, FIG. 9, or FIG. 12).

Various techniques may be used to open the switch 1302 during MRI scanning. For example, the implantable medical device may be programmable whereby an attending physician may send a command (e.g., via telemetry) to the device (e.g., to MRI controller 1308 in the device) to temporarily open the switch 1302. Alternatively, the implantable medical device may include an MRI controller 1308 (e.g., one or more MRI detectors such as a giant magneto-resistive sensor) that is configured to automatically detect the presence of MRI signals (e.g., in one or more axes). In this case, the MRI controller 1308 may automatically open the switch 1302 when an MRI signal is detected, and close to switch when the MRI signal is no longer detected.

In practice, an open solid-state switch may have significance capacitance. Consequently, such a switch may allow high frequency current pulses in response to a fast-changing voltage, similar to the feedthrough capacitor as discussed above. The aforementioned maximum allowed charge (FIG. 4A) could also be used as a guide in the design of such switches by providing a specification of maximum off-state capacitance.

It should be appreciated that the switch 1302 may be implemented in various ways. For example, the switch 1302 may be implemented before the feedthrough capacitor 1304, after the filter circuit 1306, or in some other location.

The filter circuits taught herein also may be implemented in various ways. For example, some or all of the filter circuits may be implemented as part of a feedthrough for implantable medical device and/or within the housing of the implantable medical device.

Figure 14:
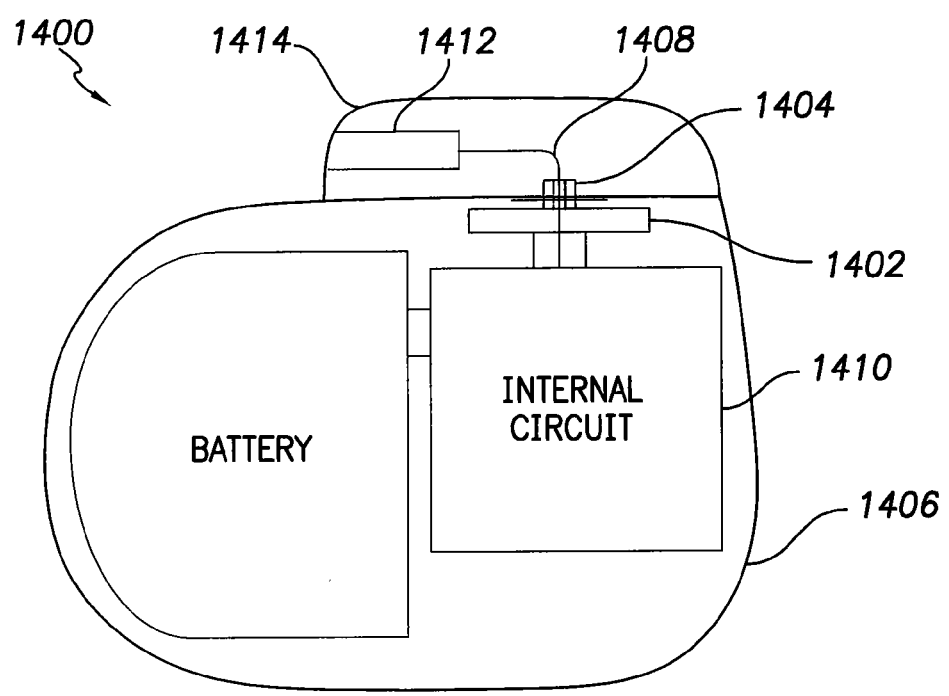
FIG. 14 is a simplified diagram of an embodiment of an implantable medical device that includes a substrate for one or more filter circuits.

FIG. 14 illustrates a sample implantable medical device 1400 where at least a portion of the filter circuitry as taught herein is implemented on a substrate (e.g., on a printed circuit board) 1402 placed immediately after a feedthrough 1404 for the implantable medical device 1400. Here, the feedthrough 1404 is hermetically sealed to the housing 1406 of the device 1400, and also provides a hermetically sealed passage for one or more conductors 1408 that enable signals be coupled between an internal circuit 1410 and an external connector 1412 (provided within a header 1414) of the device 1400. The substrate 1402 may be mounted onto the feedthrough 1404 so that the filter circuits are as close as possible to the feedthrough to reduce the amount of stray RF energy that may be radiated via the conductor(s) 1408 inside the housing 1406.

Various components may be provided on the substrate 1402. For example, in some implementations at least a portion of the feedthrough capacitance may be implemented on the substrate 1402 (e.g., instead of within the feedthrough 1404). In some implementations one or more filter circuits (e.g., one or more of filter circuits 112, 114, 604, 606, 608, 610, 704, 706, 708, 710, 902, 904, or 1306) may be implemented on the substrate 1402. In some implementations a transient surge suppressor (e.g., as described above) may be implemented on the substrate 1402. In some implementations an active switch (e.g., as described above) may be implemented on the substrate 1402.

In practice, filter circuitry for multiple channels (for multiple cardiac leads) may be implemented on the substrate 1402. Given the excellent current and voltage attenuation that may be achieved by this filter circuitry, crosstalk interference may be negligible even when a relatively small substrate having minimal PCB trace clearance is employed. It should be noted that all inductors employed in this design must have non-magnetic cores. Magnetic cores would be likely to saturate in the strong MRI static field, drastically altering inductance values.

Figure 15:
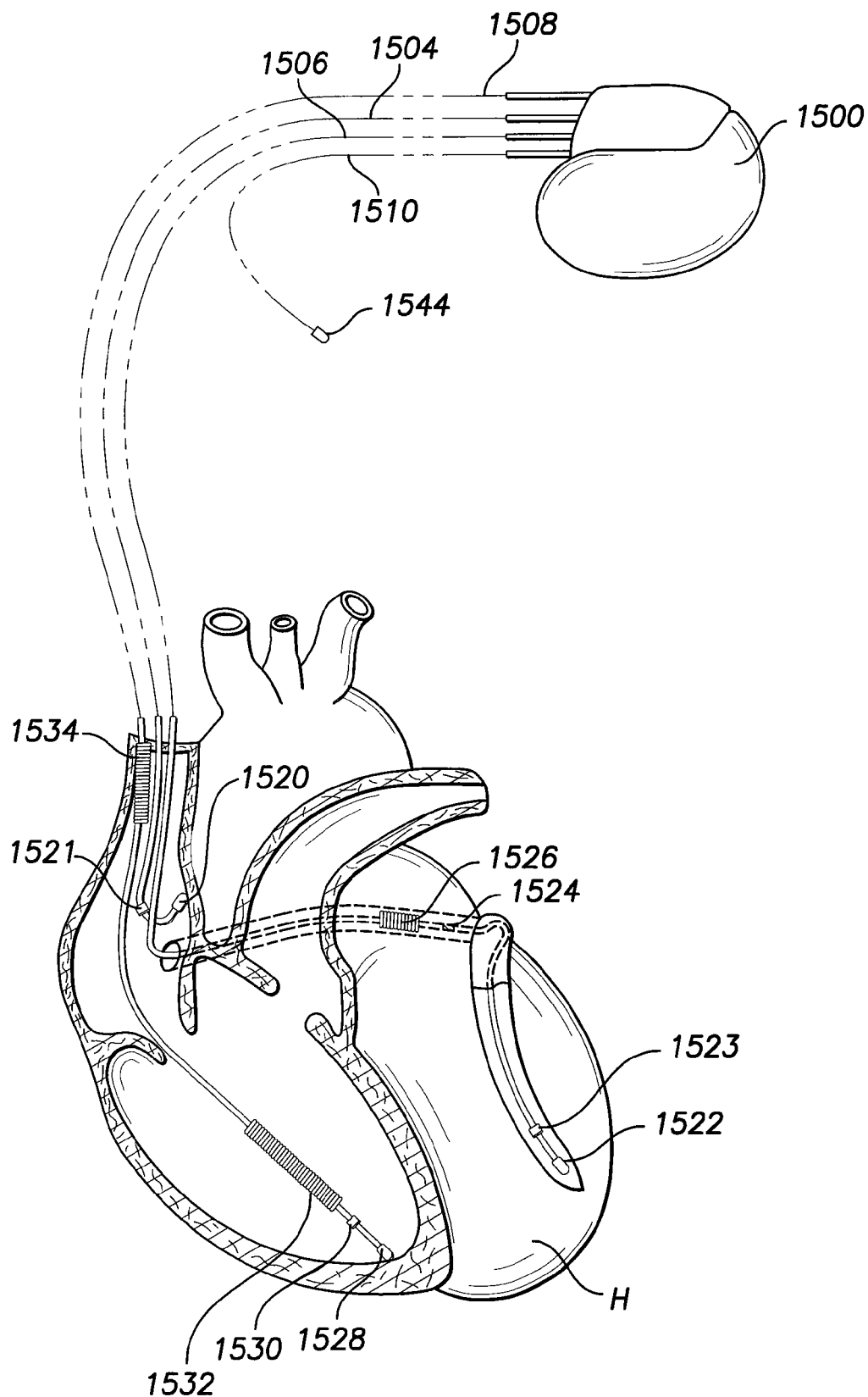
FIG. 15 is a simplified diagram of an embodiment of an implantable stimulation device in electrical communication with one or more leads implanted in a patient's heart for sensing conditions in the patient, delivering therapy to the patient, or providing some combination thereof.
Figure 16:
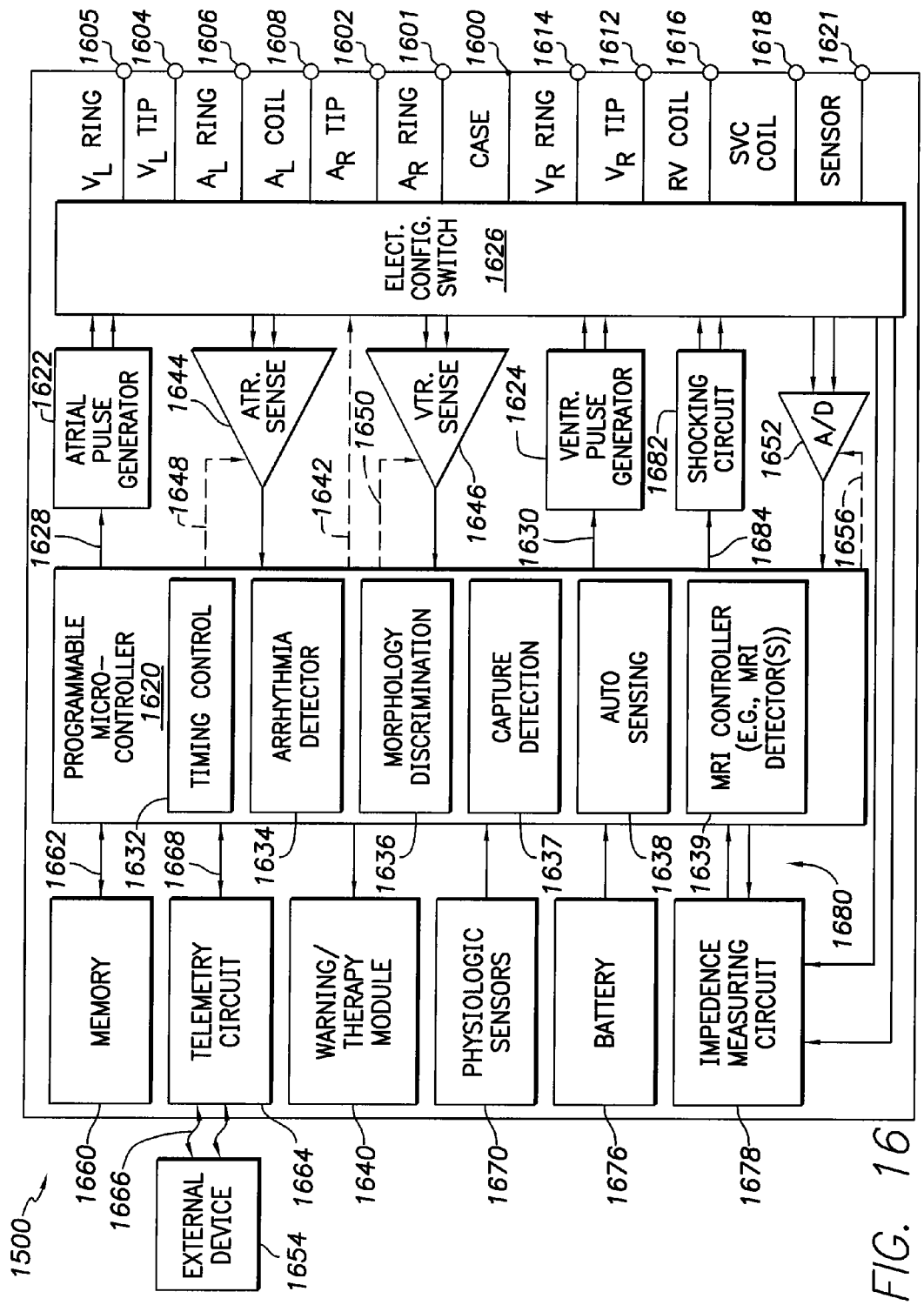
FIG. 16 is a simplified functional block diagram of an embodiment of an implantable cardiac device, illustrating basic elements that may be configured to sense conditions in the patient, deliver therapy to the patient, or provide some combination thereof.

FIGS. 15 and 16 describe an exemplary implantable medical device (e.g., a stimulation device such as a pacemaker, an implantable cardioverter defibrillator, etc.) that is capable of being used in connection with the various embodiments that are described herein. It is to be appreciated and understood that other devices, including those that are not necessarily implantable, can be used and that the description below is given, in its specific context, to assist the reader in understanding, with more clarity, the embodiments described herein.

FIG. 15 shows an exemplary implantable cardiac device 1500 in electrical communication with a patient's heart H by way of three leads 1504, 1506, and 1508, suitable for delivering multi-chamber stimulation and shock therapy. Bodies of the leads 1504, 1506, and 1508 may be formed of silicone, polyurethane, plastic, or similar biocompatible materials to facilitate implant within a patient. Each lead includes one or more conductors, each of which may couple one or more electrodes incorporated into the lead to a connector on the proximal end of the lead. Each connector, in turn, is configured to couple with a complimentary connector (e.g., implemented within a header) of the device 1500.

To sense atrial cardiac signals and to provide right atrial chamber stimulation therapy, the device 1500 is coupled to an implantable right atrial lead 1504 having, for example, an atrial tip electrode 1520, which typically is implanted in the patient's right atrial appendage or septum. FIG. 15 also shows the right atrial lead 1504 as having an optional atrial ring electrode 1521.

To sense left atrial and ventricular cardiac signals and to provide left chamber pacing therapy, the device 1500 is coupled to a coronary sinus lead 1506 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 1506 is designed to receive atrial and ventricular cardiac signals and to deliver left ventricular pacing therapy using, for example, a left ventricular tip electrode 1522 and, optionally, a left ventricular ring electrode 1523; provide left atrial pacing therapy using, for example, a left atrial ring electrode 1524; and provide shocking therapy using, for example, a left atrial coil electrode 1526 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 1500 is also shown in electrical communication with the patient's heart H by way of an implantable right ventricular lead 1508 having, in this implementation, a right ventricular tip electrode 1528, a right ventricular ring electrode 1530, a right ventricular (RV) coil electrode 1532 (or other electrode capable of delivering a shock), and a superior vena cava (SVC) coil electrode 1534 (or other electrode capable of delivering a shock). Typically, the right ventricular lead 1508 is transvenously inserted into the heart H to place the right ventricular tip electrode 1528 in the right ventricular apex so that the RV coil electrode 1532 will be positioned in the right ventricle and the SVC coil electrode 1534 will be positioned in the superior vena cava. Accordingly, the right ventricular lead 1508 is capable of sensing or receiving cardiac signals, and delivering stimulation in the form of pacing and shock therapy to the right ventricle.

The device 1500 is also shown in electrical communication with a lead 1510 including one or more components 1544 such as a physiologic sensor. The component 1544 may be positioned in, near or remote from the heart.

It should be appreciated that the device 1500 may connect to leads other than those specifically shown. In addition, the leads connected to the device 1500 may include components other than those specifically shown. For example, a lead may include other types of electrodes, sensors or devices that serve to otherwise interact with a patient or the surroundings.

FIG. 16 depicts an exemplary, simplified block diagram illustrating sample components of the device 1500. The device 1500 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

A housing 1600 for the device 1500 is often referred to as the "can", "case" or "case electrode", and may be programmably selected to act as the return electrode for all "unipolar" modes. The housing 1600 may further be used as a return electrode alone or in combination with one or more of the coil electrodes 1526, 1532 and 1534 for shocking purposes. The housing 1600 may be constructed of a biocompatible material (e.g., titanium) to facilitate implant within a patient.

The housing 1600 further includes a connector (not shown) having a plurality of terminals 1601, 1602, 1604, 1605, 1606, 1608, 1612, 1614, 1616 and 1618 (shown schematically and, for convenience, the names of the electrodes to which they are connected are shown next to the terminals). The connector may be configured to include various other terminals (e.g., terminal 1621 coupled to a sensor or some other component) depending on the requirements of a given application.

To achieve right atrial sensing and pacing, the connector includes, for example, a right atrial tip terminal (AR TIP) 1602 adapted for connection to the right atrial tip electrode 1520. A right atrial ring terminal (AR RING) 1601 may also be included and adapted for connection to the right atrial ring electrode 1521. To achieve left chamber sensing, pacing, and shocking, the connector includes, for example, a left ventricular tip terminal (VL TIP) 1604, a left ventricular ring terminal (VL RING) 1605, a left atrial ring terminal (AL RING) 1606, and a left atrial shocking terminal (AL COIL) 1608, which are adapted for connection to the left ventricular tip electrode 1522, the left ventricular ring electrode 1523, the left atrial ring electrode 1524, and the left atrial coil electrode 1526, respectively.

To support right chamber sensing, pacing, and shocking, the connector further includes a right ventricular tip terminal (VR TIP) 1612, a right ventricular ring terminal (VR RING) 1614, a right ventricular shocking terminal (RV COIL) 1616, and a superior vena cava shocking terminal (SVC COIL) 1618, which are adapted for connection to the right ventricular tip electrode 1528, the right ventricular ring electrode 1530, the RV coil electrode 1532, and the SVC coil electrode 1534, respectively.

At the core of the device 1500 is a programmable microcontroller 1620 that controls the various modes of stimulation therapy. As is well known in the art, microcontroller 1620 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 1620 includes the ability to process or monitor input signals (data or information) as controlled by a program code stored in a designated block of memory. The type of microcontroller is not critical to the described implementations. Rather, any suitable microcontroller 1620 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 16 also shows an atrial pulse generator 1622 and a ventricular pulse generator 1624 that generate pacing stimulation pulses for delivery by the right atrial lead 1504, the coronary sinus lead 1506, the right ventricular lead 1508, or some combination of these leads via an electrode configuration switch 1626. It is understood that in order to provide stimulation therapy in each of the four chambers of the heart, the atrial and ventricular pulse generators 1622 and 1624 may include dedicated, independent pulse generators, multiplexed pulse generators, or shared pulse generators. The pulse generators 1622 and 1624 are controlled by the microcontroller 1620 via appropriate control signals 1628 and 1630, respectively, to trigger or inhibit the stimulation pulses.

Microcontroller 1620 further includes timing control circuitry 1632 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 1620 further includes an arrhythmia detector 1634. The arrhythmia detector 1634 may be utilized by the device 1500 for determining desirable times to administer various therapies. The arrhythmia detector 1634 may be implemented, for example, in hardware as part of the microcontroller 1620, or as software/firmware instructions programmed into the device 1500 and executed on the microcontroller 1620 during certain modes of operation.

Microcontroller 1620 may include a morphology discrimination module 1636, a capture detection module 1637 and an auto sensing module 1638. These modules are optionally used to implement various exemplary recognition algorithms or methods. The aforementioned components may be implemented, for example, in hardware as part of the microcontroller 1620, or as software/firmware instructions programmed into the device 1500 and executed on the microcontroller 1620 during certain modes of operation.

The electrode configuration switch 1626 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 1626, in response to a control signal 1642 from the microcontroller 1620, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 1644 and ventricular sensing circuits (VTR. SENSE) 1646 may also be selectively coupled to the right atrial lead 1504, coronary sinus lead 1506, and the right ventricular lead 1508, through the switch 1626 for detecting the presence of cardiac activity in each of the four chambers of the heart. Accordingly, the atrial and ventricular sensing circuits 1644 and 1646 may include dedicated sense amplifiers, multiplexed amplifiers, or shared amplifiers. Switch 1626 determines the "sensing polarity" of the cardiac signal by selectively closing the appropriate switches, as is also known in the art. In this way, the clinician may program the sensing polarity independent of the stimulation polarity. The sensing circuits (e.g., circuits 1644 and 1646) are optionally capable of obtaining information indicative of tissue capture.

Each sensing circuit 1644 and 1646 preferably employs one or more low power, precision amplifiers with programmable gain, automatic gain control, bandpass filtering, a threshold detection circuit, or some combination of these components, to selectively sense the cardiac signal of interest. The automatic gain control enables the device 1500 to deal effectively with the difficult problem of sensing the low amplitude signal characteristics of atrial or ventricular fibrillation.

The outputs of the atrial and ventricular sensing circuits 1644 and 1646 are connected to the microcontroller 1620, which, in turn, is able to trigger or inhibit the atrial and ventricular pulse generators 1622 and 1624, respectively, in a demand fashion in response to the absence or presence of cardiac activity in the appropriate chambers of the heart. Furthermore, as described herein, the microcontroller 1620 is also capable of analyzing information output from the sensing circuits 1644 and 1646, a data acquisition system 1652, or both. This information may be used to determine or detect whether and to what degree tissue capture has occurred and to program a pulse, or pulses, in response to such determinations. The sensing circuits 1644 and 1646, in turn, receive control signals over signal lines 1648 and 1650, respectively, from the microcontroller 1620 for purposes of controlling the gain, threshold, polarization charge removal circuitry (not shown), and the timing of any blocking circuitry (not shown) coupled to the inputs of the sensing circuits 1644 and 1646 as is known in the art.

For arrhythmia detection, the device 1500 utilizes the atrial and ventricular sensing circuits 1644 and 1646 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 1634 of the microcontroller 1620 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 1652. The data acquisition system 1652 is configured (e.g., via signal line 1656) to acquire intracardiac electrogram ("IEGM") signals or other signals, convert the raw analog data into a digital signal, and store the digital signals for later processing, for telemetric transmission to an external device 1654, or both. For example, the data acquisition system 1652 may be coupled to the right atrial lead 1504, the coronary sinus lead 1506, the right ventricular lead 1508 and other leads through the switch 1626 to sample cardiac signals across any pair of desired electrodes.

The data acquisition system 1652 also may be coupled to receive signals from other input devices. For example, the data acquisition system 1652 may sample signals from a physiologic sensor 1670 or other components shown in FIG. 16 (connections not shown).

The microcontroller 1620 is further coupled to a memory 1660 by a suitable data/address bus 1662, wherein the programmable operating parameters used by the microcontroller 1620 are stored and modified, as required, in order to customize the operation of the device 1500 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 1652), which data may then be used for subsequent analysis to guide the programming of the device 1500.

Advantageously, the operating parameters of the implantable device 1500 may be non-invasively programmed into the memory 1660 through a telemetry circuit 1664 in telemetric communication via communication link 1666 with the external device 1654, such as a programmer, transtelephonic transceiver, a diagnostic system analyzer or some other device. The microcontroller 1620 activates the telemetry circuit 1664 with a control signal (e.g., via bus 1668). The telemetry circuit 1664 advantageously allows intracardiac electrograms and status information relating to the operation of the device 1500 (as contained in the microcontroller 1620 or memory 1660) to be sent to the external device 1654 through an established communication link 1666.

The device 1500 can further include one or more physiologic sensors 1670. In some embodiments the device 1500 may include a "rate-responsive" sensor that may provide, for example, information to aid in adjustment of pacing stimulation rate according to the exercise state of the patient. One or more physiologic sensors 1670 (e.g., a pressure sensor) may further be used to detect changes in cardiac output, changes in the physiological condition of the heart, or diurnal changes in activity (e.g., detecting sleep and wake states). Accordingly, the microcontroller 1620 responds by adjusting the various pacing parameters (such as rate, A-V Delay, V-V Delay, etc.) at which the atrial and ventricular pulse generators 1622 and 1624 generate stimulation pulses.

While shown as being included within the device 1500, it is to be understood that a physiologic sensor 1670 may also be external to the device 1500, yet still be implanted within or carried by the patient. Examples of physiologic sensors that may be implemented in conjunction with the device 1500 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 1670 may optionally include one or more of components to help detect movement (via, e.g., a position sensor or an accelerometer) and minute ventilation (via an MV sensor) in the patient. Signals generated by the position sensor and MV sensor may be passed to the microcontroller 1620 for analysis in determining whether to adjust the pacing rate, etc. The microcontroller 1620 may thus monitor the signals for indications of the patient's position and activity status, such as whether the patient is climbing up stairs or descending down stairs or whether the patient is sitting up after lying down.

The device 1500 additionally includes a battery 1676 that provides operating power to all of the circuits shown in FIG. 16. For a device 1500 which employs shocking therapy, the battery 1676 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 1676 also desirably has a predictable discharge characteristic so that elective replacement time can be detected. Accordingly, the device 1500 preferably employs lithium or other suitable battery technology.

The device 1500 can further include magnet detection circuitry (not shown), coupled to the microcontroller 1620, to detect when a magnet is placed over the device 1500. A magnet may be used by a clinician to perform various test functions of the device 1500 and to signal the microcontroller 1620 that the external device 1654 is in place to receive data from or transmit data to the microcontroller 1620 through the telemetry circuit 1664.

The device 1500 further includes an impedance measuring circuit 1678 that is enabled by the microcontroller 1620 via a control signal 1680. The known uses for an impedance measuring circuit 1678 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 1500 has been implanted; measuring stroke volume; and detecting the opening of heart valves, etc. The impedance measuring circuit 1678 is advantageously coupled to the switch 1626 so that any desired electrode may be used.

In the case where the device 1500 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 1620 further controls a shocking circuit 1682 by way of a control signal 1684. The shocking circuit 1682 generates shocking pulses of low (e.g., up to 0.5 J), moderate (e.g., 0.5 J to 10 J), or high energy (e.g., 11 J to 40 J), as controlled by the microcontroller 1620. Such shocking pulses are applied to the patient's heart H through, for example, two shocking electrodes and as shown in this embodiment, selected from the left atrial coil electrode 1526, the RV coil electrode 1532 and the SVC coil electrode 1534. As noted above, the housing 1600 may act as an active electrode in combination with the RV coil electrode 1532, as part of a split electrical vector using the SVC coil electrode 1534 or the left atrial coil electrode 1526 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 1620 is capable of controlling the synchronous or asynchronous delivery of the shocking pulses.

As mentioned above, the device 1500 may include several components that provide filtering-related functionality as taught herein. For example, filter circuits (not shown) may be coupled between the switch 1626 and one or more of the terminals 1605, 1604, 1606, 1602, 1601, 1614, or 1612. One or more of the switch 1626, the sense circuits 1644, 1646, and the data acquisition system 1652 may comprise the sensing circuitry discussed above. One or more of the switch 1626 and the pulse generator circuits 1622 and 1624 may comprise the cardiac stimulation circuitry discussed above.

The microcontroller 1620 (e.g., a processor providing signal processing functionality) also may implement or support at least a portion of the filtering-related functionality discussed herein. For example, an MRI controller 1639 may provide control functions as described above.

It should be appreciated that various modifications may be incorporated into the disclosed embodiments based on the teachings herein. For example, the structure and functionality taught herein may be incorporated into types of devices other than the specific types of devices described above. In addition, different filtering components and filtering schemes may be employed consistent with the teachings herein.

It should be appreciated from the above that the various structures and functions described herein may be incorporated into a variety of apparatuses (e.g., a stimulation device, a lead, a monitoring device, etc.) and implemented in a variety of ways. Different embodiments of such an apparatus may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

As used herein, terminology describing the coupling of components refers to any mechanism that allows signals to travel from one component to another. Thus, coupling may be accomplished through use of an electrical conductor and/or an electrical component (e.g., an active or passive electrical circuit). In some cases two or more components may be "directly coupled." That is, the components may be coupled via a conductor without any intervening components (e.g., an active or passive electrical circuit) between the components.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above it will be understood that the teachings herein are intended to cover any changes, adaptations or modifications which are within the scope of the disclosure.

What is claimed is:

1. An implantable medical device, comprising:
    a connector configured to receive an implantable cardiac lead;
    a cardiac stimulation circuit having a first terminal and a second terminal;
    a capacitor circuit comprising a first terminal and a second terminal, wherein the first terminal of the capacitor circuit is coupled to the connector;
    an LC tank circuit coupled between the first terminal of the capacitor circuit and the first terminal of the cardiac stimulation circuit; and
    a shunt series LC circuit coupled between the first terminal of the cardiac stimulation circuit and the second terminal of the cardiac stimulation circuit, wherein the second terminal of the cardiac stimulation circuit is coupled to the second terminal of the capacitor circuit.

2. The device of claim 1, wherein:
    the LC tank circuit has a resonant frequency that corresponds to a first MRI scanning frequency; and
    the shunt series LC circuit has a resonant frequency that corresponds to a second MRI scanning frequency that is different than the first MRI scanning frequency.

3. The device of claim 2, wherein:
    the resonant frequency of the LC tank circuit is approximately 64 MHz or approximately 128 MHz; and
    the resonant frequency of the shunt series LC circuit is approximately 64 MHz or approximately 128 MHz.

4. The device of claim 1, wherein:
    the LC tank circuit has a resonant frequency that corresponds to an MRI scanning frequency; and
    the shunt series LC circuit has a resonant frequency that is substantially equal to the resonant frequency of the LC tank circuit.

5. The device of claim 1, further comprising:
another LC tank circuit coupled between the LC tank circuit and the first terminal of the cardiac stimulation circuit; and
another shunt series LC circuit coupled between the first terminal of the cardiac stimulation circuit and the second terminal of the cardiac stimulation circuit.

6. The device of claim 1, further comprising:
another LC tank circuit coupled between the LC tank circuit and the first terminal of the cardiac stimulation circuit, wherein the LC tank circuit is coupled to the another LC tank circuit via a conductor; and
another shunt series LC circuit coupled between the conductor and the second terminal of the cardiac stimulation circuit.

7. The device of claim 1, further comprising a biocompatible housing and a feedthrough, wherein:
the feedthrough is hermetically sealed to the biocompatible housing and comprises a conductor for coupling the first terminal of the capacitor circuit to the connector; and
the capacitor circuit is incorporated in the feedthrough.

8. The device of claim 1, wherein a total equivalent capacitance value associated with the capacitor circuit and the series LC circuit is less than 3.3 nanofarads.

9. An implantable medical system, comprising:
an implantable cardiac lead comprising a first electrode; and
an implantable medical device coupled to the implantable cardiac lead, comprising:
a connector configured to receive the implantable cardiac lead;
a cardiac stimulation circuit having a first terminal and a second terminal;
a capacitor circuit coupled proximal to the first electrode;
an LC tank circuit coupled in series between the capacitor circuit and the first terminal of the cardiac stimulation circuit; and
a shunt series LC circuit coupled in parallel across the first terminal of the cardiac stimulation circuit and the second terminal of the cardiac stimulation circuit.

10. The system of claim 9, wherein:
the LC tank circuit has a resonant frequency that corresponds to a first MRI scanning frequency; and
the shunt series LC circuit has a resonant frequency that corresponds to a second MRI scanning frequency that is different than the first MRI scanning frequency.

11. The system of claim 10, wherein:
the resonant frequency of the LC tank circuit is approximately 64 MHz or approximately 128 MHz; and
the resonant frequency of the shunt series LC circuit is approximately 64 MHz or approximately 128 MHz.

12. The system of claim 9, wherein:
the LC tank circuit has a resonant frequency that corresponds to an MRI scanning frequency; and
the shunt series LC circuit has a resonant frequency that is substantially equal to the resonant frequency of the LC tank circuit.

13. The system of claim 9, wherein the implantable cardiac lead further comprises at least one other LC tank circuit.

14. The system of claim 13, wherein the at least one other LC tank circuit is incorporated into a distal portion of the implantable cardiac lead.

15. The system of claim 13, wherein each LC tank circuit of the at least one other LC tank circuit has a resonant frequency that corresponds to an MRI scanning frequency.

16. An implantable medical device, comprising:
a connector configured to receive an implantable cardiac lead;
a cardiac stimulation circuit having a first terminal and a second terminal;
a capacitor circuit coupled in parallel across the first and second terminals of the cardiac stimulation circuit;
a first series LC circuit coupled in parallel across the first and second terminals of the cardiac stimulation circuit, wherein the first series LC circuit has a first resonant frequency; and
a second series LC circuit coupled in parallel across the first and second terminals of the cardiac stimulation circuit, wherein the second series LC circuit has a second resonant frequency that is different than the first resonant frequency.

17. The device of claim 16, wherein:
the first resonant frequency corresponds to a first MRI scanning frequency; and
the second resonant frequency corresponds to a second MRI scanning frequency.

18. The device of claim 17, wherein:
the first resonant frequency is approximately 64 MHz; and
the second resonant frequency is approximately 128 MHz.

19. The device of claim 16, further comprising a transient surge suppressor coupled in parallel across the first and second terminals of the cardiac stimulation circuit, and positioned between the capacitor circuit and the first series LC circuit.

20. The device of claim 19, further comprising a resistor coupled between the transient surge suppressor and the first terminal of the cardiac stimulation circuit, and positioned between the transient surge suppressor and the first series LC circuit.

* * * * *